United States Patent
Clark et al.

(10) Patent No.: US 6,531,156 B1
(45) Date of Patent: Mar. 11, 2003

(54) AQUEOUS SOLVEN ENCAPSULATION METHOD, APPARATUS AND MICROCAPSULES

(75) Inventors: Fred M. Clark, Philadelphia, PA (US); Paul A. Offit, Bala Cynwyd, PA (US); Tully J. Speaker, Philadelphia, PA (US)

(73) Assignees: Temple University, Philadelphia, PA (US); Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/351,370

(22) Filed: Jul. 12, 1999

Related U.S. Application Data

(63) Continuation of application No. 08/809,564, filed on Mar. 24, 1997, now abandoned, and a continuation-in-part of application No. 08/228,481, filed on Apr. 15, 1994, now abandoned, and a continuation-in-part of application No. 08/229,283, filed on Apr. 18, 1994, now abandoned, and a continuation-in-part of application No. 08/229,520, filed as application No. PCT/US95/04711 on Apr. 17, 1995, now abandoned.

(51) Int. Cl.[7] .................................................. A61K 9/14
(52) U.S. Cl. ........................ 424/489; 426/490; 426/492; 426/496; 426/497; 426/499; 426/500
(58) Field of Search .................................... 424/489, 490, 424/497, 492, 493, 491, 464, 496, 499, 500

(56) References Cited

U.S. PATENT DOCUMENTS

| | | | |
|---|---|---|---|
| 2,666,759 A | 1/1954 | Wood | 260/209 |
| 2,800,457 A | 7/1957 | Green et al. | 252/316 |
| 2,800,458 A | 7/1957 | Green | 252/316 |
| 2,850,395 A | 9/1958 | Green | 106/22 |
| 3,137,631 A | 6/1964 | Soloway | 167/83 |
| 3,959,457 A | 5/1976 | Speaker et al. | 424/19 |
| 4,205,060 A | 5/1980 | Monsimer et al. | 424/14 |
| 4,352,883 A | 10/1982 | Lim | 435/178 |
| 4,606,940 A | 8/1986 | Frank et al. | 427/213.32 |
| 4,636,385 A | 1/1987 | Plotkin et al. | 424/89 |
| 4,743,583 A | 5/1988 | Speaker et al. | 514/4 |
| 4,744,933 A | 5/1988 | Rha et al. | 264/4.3 |
| 4,789,516 A | 12/1988 | Lim | 264/4.32 |
| 4,797,234 A | 1/1989 | Speaker et al. | 264/4.1 |
| 4,886,663 A | 12/1989 | Houghten | |

(List continued on next page.)

FOREIGN PATENT DOCUMENTS

| | | |
|---|---|---|
| BE | 882476 | 9/1980 |
| EP | 0 266 119 | 5/1988 |
| EP | 0 299 205 | 1/1989 |
| EP | 0 333 523 | 9/1989 |
| GB | 2 135 954 A | 9/1984 |
| WO | WO 90/00048 | 1/1990 |
| WO | WO 93/01806 | 2/1993 |

OTHER PUBLICATIONS

Andrade et al, "Coated Adsorbents for Direct Blood Transfusion: HEMA/activated Carbon", Trans. Amer. Soc. Artif. Int. Organs 17:222–228 (1971).

Claassen and Osterhaus, "The Iscom Structure as an Immune–Enhancing Moiety: Experience with Viral Systems", Res. Immunol. 143:531–541 (1992).

Clark et al, "Immune Response of Infants and Children to Low–Passage Bovine Rotavirus (Strain WC3)", Am. J. Dis. Child. 140:350–356 (1986).

Edelman et al, "Immunization of Rabbits with Enterotoxigenic *E. coli* Colonization Factor Antigen (CFA/I) Encapsulated in Biodegradable Microspheres of Poly–(Lactide–C-o–Glycolide)", Vaccine 11:155–158 (1993).

(List continued on next page.)

*Primary Examiner*—Thurman K. Page
*Assistant Examiner*—Liliana Di Nola-Baron
(74) *Attorney, Agent, or Firm*—Nixon & Vanderhye PC

(57) ABSTRACT

The present invention relates to microcapsules comprising a wall and an aqueous core comprising various active agents, and prepared by the interfacial reaction in aqueous medium of Lewis acid and base wall-forming reactants.

10 Claims, 1 Drawing Sheet

U.S. PATENT DOCUMENTS

| | | | | |
|---|---|---|---|---|
| 4,923,645 | A | * 5/1990 | Tsang et al. | 264/4.3 |
| 5,075,109 | A | 12/1991 | Tice et al. | |
| 5,093,198 | A | 3/1992 | Speaker et al. | 428/402.21 |
| 5,132,117 | A | 7/1992 | Speaker et al. | 424/490 |
| 5,190,877 | A | 3/1993 | Osinga | 435/256 |
| 5,227,298 | A | 7/1993 | Weber | 435/178 |
| 5,284,663 | A | 2/1994 | Speaker | |
| 5,306,492 | A | 4/1994 | Porro | |
| 5,622,656 | A | 4/1997 | Huc | 264/4.3 |
| 5,686,113 | A | * 11/1997 | Speaker et al. | 424/490 |

OTHER PUBLICATIONS

Eldridge et al, "Biodegradable and Biocompatible Poly(DL–Lactide–Co–Glycolide) Microspheres as an Adjuvant for Staphylococcal Enterotoxin B Toxoid Which Enhances the Level of Toxin–Neutralizing Antibodies", Infect. Immun. 59:2978–2986 (1991).

Eldridge et al, "Vaccine–Containing Biodegradable Microspheres Specifically Enter the Gut–Associated Lymphoid Tissue Following Oral Administration and Induce a Disseminated Mucosal Immune Response", Immunobiology of Proteins and Peptides V Vaccines: 191–202 Ed. Atassi, Plenum Press, New York (1989).
Eldridge et al, "Controlled Vaccine Release in the Gut–Associated Lymphoid Tissues. I. Orally Administerd Biodegradable Microspheres Target the Peyer's Patches", J. Controlled Release 11:205–214 (1990).
Eldridge et al, "Biodegradable Microspheres as a Vaccine Delivery System", Mol. Immunol. 28:287–294 (1991).
Eldridge et al, "Biodegradable Microspheres: Vaccine Delivery System for Oral Immunization", Curr. Top. Microbiol. Immunol. 146:59–66 (1989).
Gerlier et al, "Liposomes as a Tool to Study the Role of Membrane Presentation in the Immunogenicity of a MuLV–Releated Tumor Antigen", J. Immunol. 131:485–490 (1983).
Ito et al, "Void Structure in Colloidal Dispersions", Science 263:66–68 (1994).
Kowk et al, "Production of 5–15 $\mu$m diameter alginate polylysine microcapsules by an Air Atoization Technique", Pharm. Res. 8:341–344 (1991).
Levy et al, "Fourier Transform Infrared Spectroscopic Studies fo Human Serum Albumin Microcapsules Prepared by Interfacial Cross–linking with Terephthaloylchloride: Influence of Polycondensation pH on Spectra and Relation with Microcapsule Morphology and Size", J. Pharm. Sci. 80:578–585 (1991).
Lim and Sun, "Microencapsulated Islets as Bioartificial Endocrine Pancreas", Science 210:908–910 (1980).
Marx et al, "Protection Against Vaginal SIV Transmission with Microencapsulated Vaccine", Science 260:1323–1327 (1993).
Mathews and Nixon, "Surface Characteristics of Gelatin Microcapsules by Scanning Electron Microscopy", J. Pharm. Pharmacol. 26:383–384 (1984).
Miller et al, "Vaccination of Rhesus Monkeys with Synthetic Peptide in a Fusogenic Proteoiposome Elicits Simian Immunodeficiency Virus–Specific $CD8^+$ Cytotoxic T Lymphocytes", J. Exp. Med. 176:1739–1744 (1992).
Moldoveanu et al, "Oral Immunization with Influenza Virus in Biodegradable Microspheres", J. Infect. Dis. 167:84–90 (1993).
O'Hagan et al, "Biodegradable Microparticles as Controlled Release Antigen Delivery Systems", Immunology 73:239–242 (1991).
O'Hagan et al, "Biodegradable Microparticles for Oral Immunization", Vaccine 11:149–154 (1993).
Offit et al, "The Cultivation of Human Rotavirus, Strain 'Wa', to High Titer in Cell Culture and Characterization of the Viral Structural Polypeptide", J. Virol. Methods 7:29–40 (1983).
Offit et al, "Response of Mice to Rotaviruses of Bovine and Primate Origin Assessed by Radioimmunoassay, Radioimmunoprecipitation, and Plaque Reduction Neutralization", Infect. Immun. 42:293–300 (1983).
Ray et al, "Microencapsulated Human Parainfluenza Virus Induces a Protective Immune Response", J. Infect. Dis. 167:752–755 (1993).
Reddy et al, "Liposomes as antigen Delivery Systems in Viral Immunity", Sem. Immunol. 4:91–96 (1992).
Reid et al, "Colonization Factor Antigen/II (CDA/II) Incorporated Into Biodegradable, Biocompatible Microspheres as an Intestinal Vaccine Against Enterotoxigenic *E. Coli* (ETEC): A Safety, Immunization, and Efficacy Human Study", (Abstract) J. Immunol. 150:323A (1993).
Reid et al, "Preclinical Evaluation of Microencapsulated CFA/II Oral Vaccine Against Enterotoxigenic *E. Coli*", Vaccine 11:159–167 (1993).
Santiago et al, "Oral Immunization of Rats with Proteinoid Microspheres Encapsulating Influenza Virus Antigens", Pharm. Res. 10:1243–1247 (1993).
Singh et al, "Controlled Delivery of Diphtheria Toxoid Using Biodegradable Poly(d,L–Lactide) Microcapsules", Pharm. Res. 8:958–961 (1991).
Clark et al, "Immune Protection of Infants Against Rotavirus Gastroenteritis by a Serotype 1 Reassortant of Bovine Rotavirus WC3", J. of Infectious Diseases 161:1099–1104 (1990).
Clark et al, "Protective Effect of WC3 Vaccine Against Rotavirus Diarrhea in Infants During a Predominantly Serotype 1 Rotavirus Season", J. Infectious Diseases 158:570–587 (1988).
Benjamin, "Mechanism and Dynamics of Ion Transfer Across a Liquid–Liquid Interface", Science 261:1558–1560 (1993).
Galley and Hieftje, "Techniquej for Producing Capillaries with Reproduceable Orifice Diameters for Uniform Droplet Generation", Applied Spectroscopy 46:1460–1463 (1992).
Georges–Courbot et al, "Evaluation fo the Efficacy of a Low–Passage Bovine Rotavirus (Strain WC3) Vaccine in Children in Central Africa", Res. Virol. 142:405–411 (1991).
Weiss and Clark, "Rapid Inactivation of Rotaviruses by Exposure to Acid Buffer or Acidic Gatric Juice", J. Gen. Virol. 66:2725–2730 (1985).
Shafi et al, "Albumin Microspheres: Tissue Distribution after Oral Administration to Rats", $8^{th}$ International Symposium on Microencapsulation, Dublin, Ireland Sep. 16–19, 1992.
Ghosal et al, "Standardization of a Newly Designed Vibrating Capillary Apparatus for the Preparation of Microcapsules", Chem. Eng. Technol. 16:395–398 (1993).
Starn and Hieftje, "Accoustically Driven Device for Introducing Solid Samples Into an Inductively Coupled Plasma", Applied Spectroscopy 46:1454–1459 (1992).
Gould–Fogerite and Mannino, "Targeted Fusogenic Proteoliposomes: Functional Reconstitution of Membrane Proteins Through Protein–Cochleate Intermediates", Liposome Technology vol. III, Gregoriadis (ed. CRC Press, Boca Raton, FL) Chapter 17, pp. 262–276 (1992).

* cited by examiner

AQUEOUS SOLVEN ENCAPSULATION METHOD, APPARATUS AND MICROCAPSULES

This is a continuation of application Ser. No. 08/809,564, filed Mar. 24, 1997, now abandoned; which is a 371 of PCT/US95/04711, filed Apr. 17, 1995, which is a continuation in part of Ser. No. 08/228,481, filed Apr. 15, 1994, and a continuation-in-part of 08/229,283, filed Apr. 18, 1994, and a continuation-in-part of Ser. No. 08/229,520, filed Apr. 18, 1994, all now abandoned.

CROSS REFERENCE TO RELATED APPLICATIONS

FIELD OF THE INVENTION

The present invention relates to novel microcapsules having an anisotropic salt membrane encapsulating an aqueous or substantially aqueous core which may comprise various active agents. The microcapsules are prepared by the interfacial reaction, in aqueous medium, of Lewis acid and base wall-forming reactants.

BACKGROUND OF THE INVENTION

Microencapsulation is a process by which a relatively thin coating can be applied to dispersions of small particles of solids or droplets of liquids, thus providing a means for converting liquids to solids, altering colloidal and surface properties, providing environmental protection, and controlling the release characteristics or availability of coated materials. Several of these properties can be attained by macropackaging techniques; however, the uniqueness of microencapsulation is the smallness of the coated particles and their subsequent use and adaptation to a wide variety of dosage forms and product applications. Heretofore, known feasible methods for producing microcapsules on an industrial scale have often involved the use of organic solvents. However, the use of organic solvents may present environmental and safety problems. In addition, it is often difficult to remove all the organic solvent from the microcapsules, thus leaving organic contaminants.

It has been proposed to use microcapsules as a means of delivering vaccine. Two broad types of antigen delivery systems have been studied for their capacity to enhance immunity: solid (or porous) microcapsules and microcapsules with a core region surrounded by a physically distinct wall. Solid is microcapsules may be prepared by a variety of processes including coacervation of colloids (Kwok, K. K., et al., 1991, *Pharm. Res.*, 8: 341–344), precipitation of proteins by physical means (e.g., phase separation) or chemical agents (e.g., acid chlorides) (Levy, M. C., et al., 1991, *J. Pharm. Sci.*, 80: 578–585), or solvent evaporation techniques that surround aqueous dispersions with polyester films (Singh, M. et al., 1991, *Pharm. Res.*, 8: 958–961). Wall/core systems shown useful for antigen delivery include liposomes (Gerlier, D. et al., 1983, *J. Immunol.*, 131: 490), ISCOMS (Claasen, I., and Osterhaus, A., 1992, *Res. Immunol.*, 143: 531–541) and proteosomes (Gould-Fogerite, S. and Mannino, R., 1992, *Liposome Technology, Volume III*, Gregoriadis, G., (ed.), CRC Press, Boca Ration, Fla.; Miller, M. D. et al., 1992, *J. Exp. Med.*, 176: 1739–1744).

Perhaps the best studied of the antigen delivery systems are those derived from the linear polymeric esters of lactic acid and glycolic acid (i.e., poly (DL-lactide-co-glycolide)) (PLCG) (Edelman, R. et al., 1993, *Vaccine*, 11: 155–158; Eldridge, J. H. et al., 1989, *Curr. Top. Microbiol. Immunol.*, 146: 59–66; Eldridge, J. H. et al., 1990, *J. Controlled Release*, 11: 205–214; Eldridge, J. H. et al., 1989, *Adv. Exp. Med. Biol.*, 251: 191–202; Eldridge, J. H. et al., 1991, *Mol. Immunol.*, 28: 287–294; Eldridge, J. H. et al., 1991, *Infect. Immun.*, 59: 2978–2986; Marx, P. A. et al., 1993, *Science*, 260: 1323–1327; Moldoveanu, Z. et al., 1993, *J. Infect. Dis.*, 167: 84–90; O'Hagan, D. T. et al., *Vaccine*, 11: 149–154; O'Hagan, D. T. et al., 1991, *Immunology*, 73: 239–242; Ray, R. et al., 1993, *J. Infect. Dis.*, 167: 752–755; Reid, R. et al., 1993, *J. Immunol.*, 150: 323A; Reid, R. H. et al., 1993, *Vaccine*, 11: 159–167). Encapsulation of putative antigens into PLCG microcapsules affords a number of advantages. First, microcapsules are easily degraded by hydrolysis to form lactic acid and glycolic acid. Second, PLCG microcapsules less than 5 μm in size readily penetrate Peyer's patches, mesenteric lymph nodes and spleen after oral inoculation of mice. Third, oral intraperitoneal, intranasal or subcutaneous inoculation of mice with PLCG microencapsulated antigens including influenza virus, parainfluenza virus, simian immunodeficiency virus, Staph. aureus enterotoxin B toxoid, and ovalbumin induces a greater immune response than that induced in animals inoculated with the same dose of free virus or protein. In addition, oral inoculation of mice with inactivated viruses induces an enhanced antigen-specific IGa response at mucosal surfaces. Lastly, PLCG microcapsules have been administered orally to adult volunteers without adverse effects.

The major disadvantage of PLCG microcapsules is the requisite use of organic solvents. Contact with organic solvents tends to inactivate the infectivity of viral and bacterial pathogens, and, in addition, may alter the immunogenicity of surface proteins critical to induction of humoral or cellular immune responses. In fact, large quantities of viral proteins have been required to induce an antigen-specific immune response with PLCG microcapsules.

U.S. Pat. No. 3,137,631 relates to encapsulation of water insoluble organic liquids by cross-linking synthetic resins through the application of heat or catalysts or both. The capsule shells are described as formed from covalently linked non-ionic materials or from heat denaturable proteins. The resultant capsules benefit from secondary treatment with cross-linking agents to impart increased stability to the capsule.

U.S. Pat. No. 4,205,060 discloses microcapsules comprising a core containing a water soluble salt formed by reaction between a polymeric ionic resin and a medicament, formed either by reaction of an acidic polymer with a basic medicament or, conversely, a basic polymer with an acidic drug. The walls of the microcapsules are formed from water-insoluble film-forming polymers. The water-insoluble film-forming polymers identified as suitable sheathing agents are all neutral non-ionized polymers. The capsules of that invention are made by preparing an aqueous solution of a salt made by reacting a medicament and a core polymer; preparing a solution of a water-insoluble sheath-forming polymer in a first water-immiscible organic liquid; dispersing the aqueous solution in the organic solution; and adding to the dispersion a second water-immiscible liquid which is a non-solvent for the sheath-forming polymer to precipitate the film around droplets of the dispersed aqueous phase.

U.S. Pat. No. 4,606,940 discloses the preparation of microcapsules by coacervation to precipitate the encapsulating material. A single colloid is dispersed in water and the water of salvation is removed from around the colloid by addition of chemical compounds which have a greater affinity for water than the colloid. This causes the colloid chains to come closer together and form the coacervate. Temperature changes are needed to facilitate the encapsulation by coacervation.

U.S. Pat. No. 3,959,457 discloses microcapsules comprised of the reaction product produced in a finely dispersed emulsion of a water-immiscible solution of (a) an organic polyfunctional Lewis base, in a (b) low boiling point, polar, organic solvent, and an aqueous solution of a (c) partially hydrophilic, partially lipophilic, polyfunctional Lewis acid. The capsules of that invention have lipophilic cores.

U.S. Pat. No. 5,132,117 discloses microcapsules that consist of aqueous or substantially aqueous cores surrounded by capsular anisotropic Lewis salt membranes. These aqueous-core microcapsules are prepared by dispersing an aqueous solution of a suitable Lewis-acid wall-forming reactant and a core material in a suitable non-aqueous solvent, adding an additional amount of non-aqueous solvent containing a suitable Lewis-base wall-forming reactant, and harvesting the microcapsules formed by the interfacial reaction. Alternatively, the aqueous-core microcapsules of that patent may be prepared by dispersing an aqueous solution of a suitable Lewis-acid wall-forming reactant and a core material in a suitable non-aqueous solvent containing a suitable Lewis-base wall-forming reactant and harvesting the microcapsules formed by the interfacial reaction.

F. Lim, in Belgium Patent No. 882,476, (1980), describes a process in which calcium alginate microspheres are first formed, then surface treated to convert them to poly-lysine or poly-ethylenimine alginate coacervates and finally core-liquified by treatment with a calcium chelating agent.

Rha and Rodriques-Sanchez, in U.S. Pat. No. 4,744,933 (1988), simplify the Lim procedure by spraying one charged polymer directly into an oppositely charged polymer to produce a complex coacervate similar to that of Lim.

Dautzenberg et al., in U.K. Patent Application 2 135 954 A (1984), similarly describe formation of complex coacervate microcapsules by forcing 2 to 3 mm droplets of anionic polymer solutions to fall several tens of centimeters into solutions of oppositely charged poly-quaternary ammonium salts. In all of these other methods, it is clear that high viscosity polymer solutions are required to produce microcapsules effectively, and all employ two oppositely charged polymers to form complex coacervates.

Ito et al., Science, 263:66–68 (1994) have used time lapse confocal laser micrographs to demonstrate the tendency toward inhomogeneity of colloidal solutions of anionic polymers, such as sodium polyacrylate, with the development of some microregions of relatively high polymer concentrations and other regions with no polymer.

The present invention provides microencapsulation technology analogous to that described above with reference to U.S. Pat. Nos. 3,959,457 and 5,132,117, but different in that it utilizes an all aqueous system. The microcapsules of this invention are based on formation of poorly soluble (amine) salts of polyanionic macromolecules. This process is capable of producing uniform size particles under very gentle conditions.

By contrast, many of the previously known entirely aqueous systems are based on formation of coacervates, either simple or complex, and provide microbeads of widely ranging particle size. B. R. Mathews and J. R. Nixon, Surface characteristics of gelatin microcapsules by scanning electron microscopy, *J. Pharzm. Pharmacol.* 26:383–384 (1974). Some simple coacervates suffer from the disadvantage of requiring strongly acid (e.g. pH 3–4) media to precipitate proteinaceous coacervates. Complex coacervates precipitated from aqueous solution require at least two oppositely charged polymers. Entirely aqueous systems for preparation of hydrogels based on hydroxyethylacrylate involve free radical polymerization catalyzed by per-oxy species or ionizing radiation. J. D. Andrade, D. Gough, B. Kolff, W. J. Kunitomo and R. V. Wagenon, Coated adsorbents for direct blood transfusion: HEMA/activated carbon, *Trans. Amer. Soc. Artif. Int. Organs* 17:222–228 (1971). Such catalysts are likely to be destructive of fragile protein molecules or intact organisms. It is known that hydrogels prepared from aqueous alginic acid and calcium ion can be made in a process gentle enough to embed and preserve live for later release both microbes and multicellular organisms (e.g., nematodes). F. Lim and A. M. Sun, *Science* 210:908–910 (1980). Moreover, the calcium alginate system appears to be limited to that single alginate salt, and would not provide the amine salts of the present invention.

A number of recent papers describe other means to encapsulate immunogenic materials but rely on non-aqueous systems. J. H. Eldridge et al. (1991) *Molecular Immunology* SUPRA., R. Edelman, et al. (1993) Vaccine SUPRA., and R. Reddy, S. Nair, K. Byrnestad and B. T. Rouse, Liposomes as antigen delivery systems in viral immunity. *Sem. Immunol.* 4:91–96 (1992). Immunogenic subunit vaccine components have been captured in poly-acrylate and poly-glycolide/lactide beads or liposome-like vesicles through processes utilizing volatile organic solvents such as dichloromethane or chloroform. The solvents are used to form emulsions of polymer solution or dried lipid films. Poly-acrylate and poly-glycolide/lactide processes typically result in microbeads with extremely low (approximating 0.01%) immunogen or antigen capture efficiency compared to the relatively higher (approximating 5%) efficiency seen in the present, not yet optimized, process.

Thus, there remains a need for effective systems for microencapsulation of active agents, and immunogenic substance in particular.

SUMMARY OF THE INVENTION

According to one aspect, the present invention provides stable microcapsules that have aqueous cores and are substantially free of non-aqueous contaminants. The microcapsules may advantageously comprise an active agent. The invention further provides a highly efficient method of preparing such microcapsules.

This invention also provides means for encapsulating materials using an entirely aqueous system of reagents at or below room temperature and without need for high pressures. As such, it has application to many substances or entities which are unstable to the organic solvents, elevated temperatures, and/or high pressures heretofore employed in most encapsulation systems. Most notable among such substances and entities are naturally occurring or biotechnologically derived enzymes, proteins and peptides such as glucose 6-phosphate dehydogenase, calcitonin, erythropoietin, hemoglobin, insulin, interleukin, or somatotropin, naturally occurring non-proteinaceous macromolecules such as heparin, vaccines and vaccine components derived from intact or immunogenic subunits including "naked" desoxyribonucleic acid (DNA) and desoxyribonucleic acid constructs, and/or derived from intact or attenuated organisms or their immunogenic subunits including actinomyces, bacilli, cocci, fungi, helminths, larvae, prions, protozoa, rickettsia, spirochetes, viruses, multicellular parasites and yeasts, tolerizing antigens used for immunization against or attenuation of allergic responses to dusts, danders, pollens, spores and the like, and cells such as pancreatic islet cells, hepatocytes, interleukin- and other immunomoudulator-secreting cells derived from human or other species when implated to serve as surrogates for damaged, dysfunctional or missing tissues and/or organs which, if not encapsulated, might be recognized as foreign to the recipient organism and subject to unwanted immunologic attack.

This invention further provides means for encapsulating and later releasing highly irritant drugs, such as fluorouracil, at a rate slow enough to reduce the toxicity of such agents, as well as to encapsulate, release slowly, and sustain uniform therapeutic concentrations of numerous drugs (typified by anti-inflammatory agents such as prednisolone and indomethacin, antibodies such as tetracycline or antispasmodic drugs such as theophylline). When used to encapsulate pigmented or opaque materials such as blue dextran or charcoal, the system may be used to photoprotect bioactive agents such as ivermectin (an ectoparasiticide) and Bt proteins (*Bacillus thuringiensis* larvacidal proteins) which are unstable to light, and to release such agents either gradually or in triggered bursts. Fluorescently labelled microcapsules may be made and used to color code, identify, or aid in detecting and locating encapsulated formulations.

According to another aspect, the present invention provides encapsulated rotavirus particles, and other such agents which are typically unstable and/or denatured by organic solvents, elevated temperatures, and/or high pressures heretofore employed in most encapsulation systems. The rotavirus which are encapsulated according to the present invention include reassortant strains of rotavirus which are particularly useful as vaccines to protect against rotavirus infection.

As will appear from the following description, the present invention enables vaccine delivery in a way which allows for penetration of antigen into mucosal lymphocyte populations (e.g., Peyer's patch) after oral inoculation, as well as persistence of antigen in tissues after oral or parenteral inoculation.

BRIEF DESCRIPTION OF THE FIGURE

The accompanying

DETAILED DESCRIPTION OF THE INVENTION

Figure 1:
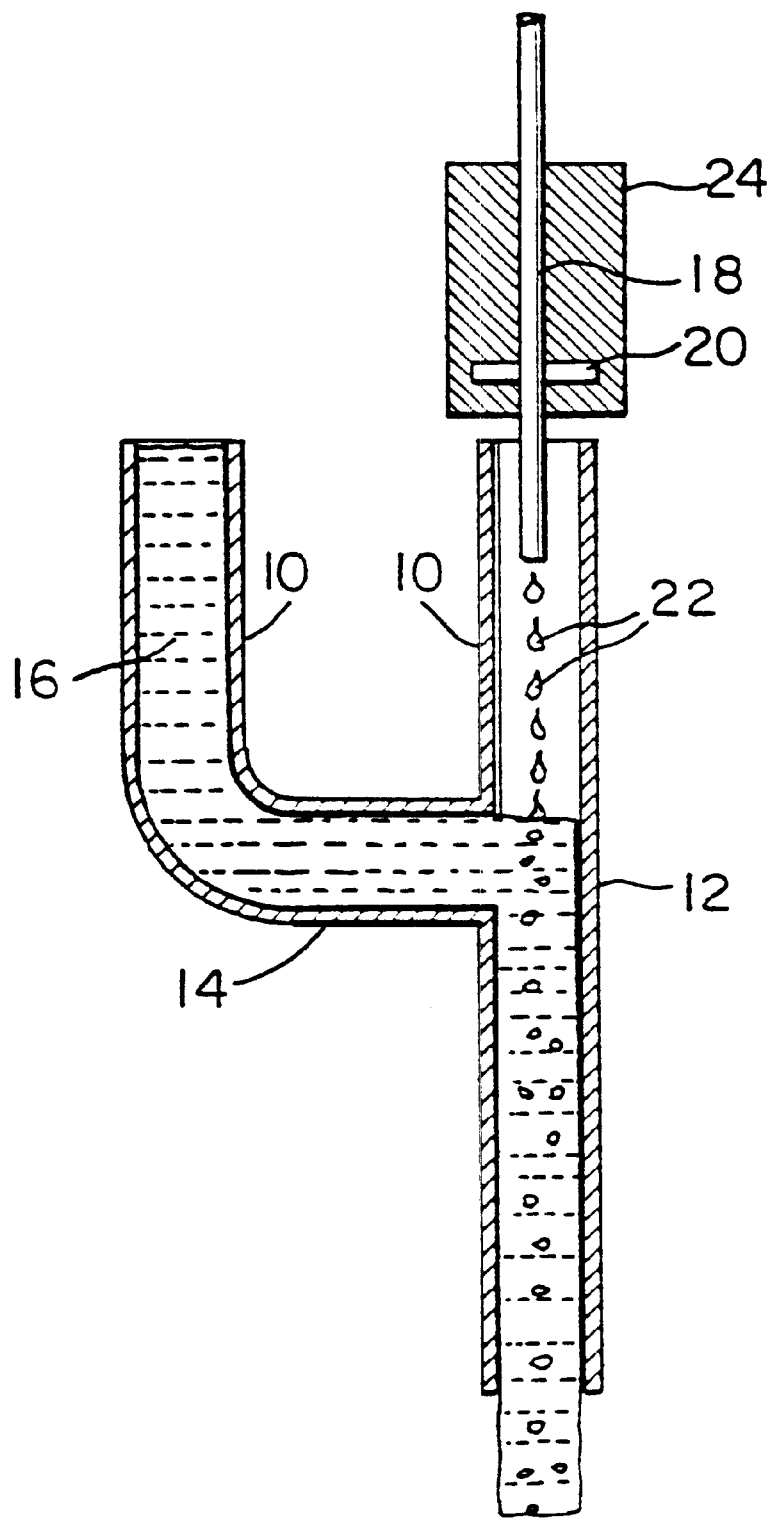
FIG. 1 is a schematic side view of an apparatus used in the preferred method for making the microcapsular material of the present invention.

The Lewis salt-walled aqueous-cored microcapsules of this invention are prepared as described below. The encapsulation system employs the essentially instantaneous reaction between droplets of aqueous solutions of anionic polymers or their water soluble salts and aqueous solutions of low molecular weight cationic amine reactants or their water soluble salts to form water insoluble films around the droplets and their contents. The capsular membrane of the resultant microcapsules is an ionically-stabilized, anisotropic Lewis salt membrane.

An aqueous solution or suspension of active agent (e.g., drug, vaccine or pesticide) and, if desired, adjuvant (photoprotectant, colorant), is dissolved or suspended in an aqueous solution of (e.g., the sodium salt of) a suitable poly-anionic macromolecule (i.e., polymer). Then the resulting solution/suspension is dispersed as droplets in an aqueous solution of (e.g., the hydrochloride salt of) a suitable water soluble amine. At the apparent interface of the polymer droplets and amine solution, a salt exchange reaction takes place to result in the formation of a very poorly soluble salt (formed between the amine and polymer) which precipitates to form more or less spherical beads or capsules in which active component is captured. The resulting suspension of microcapsules containing encased active component is collected.

Although various active agents may be microencapsulated in accordance with this invention, the invention will be described below primarily with reference to microencapsulation of immunogenic agents, and particularly rotavirus. Thus, according to one embodiment, the present invention enables delivery of immunogenic agents useful as prophylactic immunizing agents, i.e., vaccines, and/or immunotherapeutics.

As used herein, the term "immunogenic composition" includes: immunogenic peptides and proteins including mixtures comprising immunogenic peptides and/or proteins; intact inactive, attenuated and infectious viral particles; intact killed, attenuated and infectious prokaryotes; intact killed, attenuated and infectious protozoans including any life cycle stage thereof, and intact killed, attenuated and infectious multicellular pathogens. In some embodiments, strains of viruses represented by the envelope and non-envelope viruses may be used to provide microencapsulated vaccines.

Immunogenic peptides and proteins include peptides and proteins which comprise at least an epitope identical or substantially similar to an epitope displayed on an antigen against which an immune response is desired. In some preferred embodiments, immunogenic peptides and proteins are identical to naturally occurring peptides and proteins from pathogens or cells against which an immune response is desired. The proteins may be derived from pathogens such as viruses, prokaryotes, protozoan pathogens and multicellular parasites. In addition, other immune targets may also be provided such as proteins associated with tumors and autoimmune diseases. Proteins are purified from natural sources or produced using recombinant DNA techniques. In preferred embodiments, the immunogenic peptides and proteins are pathogen proteins such as viral coat proteins, prokaryotic outer membrane proteins or other antigenic proteins against which a pathogen neutralizing immune response can be invoked. Such microencapsulated peptides and proteins are microencapsulated subunit vaccines.

As used herein, the term "substantially similar epitope" is meant to refer to an epitope that has a structure which is not identical to an epitope of a protein but nonetheless evokes a cellular or humoral immune response which cross reacts to that protein.

Immunogenic peptides and proteins include mixtures which include such components in addition to other immunogenic peptides and proteins and/or non-immunogenic components. Mixtures may be obtained by partial purification of immunogenic peptides and proteins from starting materials which include other components.

Viral vaccines are well known and include: inactive or "killed" virus particles; attenuated viral particles whose infectious capabilities are compromised for example, through recombinant insertions, deletions or insertions or by selective passaging techniques; infectious virus used against other species or as recombinant vectors to deliver and express genes encoding immunogenic proteins. In some embodiments, strains of viruses represented by the envelope and non-envelope viruses may be used to provide microencapsulated vaccines.

Similarly, prokaryotic vaccines are well known and include: killed organisms; attenuated organisms whose infectious capabilities are compromised; infectious organisms including recombinant vectors to deliver and express genes encoding immunogenic proteins.

In the case of recombinant vectors, the proteins encoded by the genes inserted into the vector are immune targets. Examples of immune targets include but are not limited to pathogen proteins such as proteins from viruses, prokaryotes, protozoan pathogens and multicellular parasites or proteins associated with tumors and autoimmune diseases.

Vaccines against protozoan pathogens using intact killed or attenuated protozoan organisms generally use the organism at a life stage in which the vaccinated organism is normally a host to ensure that the proper immune targets are displayed.

It is also contemplated that in addition to delivery of vectors for the production of immunogenic proteins, microencapsulated vectors may also be provided in gene therapy applications in which the vector carries a therapeutic gene which encodes a non-immunogenic proteins. Such vectors include but are not limited to viral vectors such as recombinant retroviruses and recombinant adenoviruses.

According to another embodiment, the present invention provides microencapsulated rotavirus useful for delivery as prophylactic immunizing agents, i.e., rotavirus vaccines.

Rotavirus vaccines are well known and include: Bovine WC3 (ATCC accession number VR-2102); HCR3a (ATCC accession number VR-2325 deposited May 1, 1991); Bovine WC3, modified with Human vp4 W179; Bovine WC3, modified with Human W178-8; Bovine WC3, modified with Human W179-9 (ATCC accession number VR-2194 and VR-2196 deposited Nov. 25, 1987) or SC2-9 (ATCC accession number VR-2417 deposited Jul. 8, 1993); Bovine WC3, modified with Human WI79-9 (ATCC accession number VR-2415 deposited Jul. 8, 1993) and WI79-4 (ATCC accession number VR-2377 deposited Jun. 19, 1992); Bovine WC3, modified with Human vp4 DS1 (ATCC accession number VR-2416 deposited Jul. 8, 1993); Bovine WC3, modified with Human Bricout B-9; Bovine WC3, modified with Human vp4 Bricout A; HCR3a, modified with Human W179-9 (ATCC accession number VR-2324 deposited May 1, 1991); Rhesus rotavirus RRV; RRV modified with Human Wa-9; RRV modified with Human DS1-9; RRV modified with Human P-9; and RRV modified with Human ST3-9.

Rotavirus strains useful according to the present invention include those described in: U.S. Pat. No. 4,636,385 issued Jan. 13, 1987; U.S. patent application Ser. No. 07/126,477, filed Nov. 30, 1987; U.S. patent application Ser. No. 07/588,884, filed Jul. 26, 1990; U.S. patent application Ser. No. 07/694,968, filed May 1, 1991; and U.S. patent Application Ser. No. 07/902,321, filed Jun. 22, 1992, each of which is incorporated herein by reference.

An aqueous solution or suspension of immunogenic compositions is dissolved or suspended in an aqueous solution of (e.g., the sodium salt of) a suitable poly-anionic macromolecule (i.e., polymer). Then the resulting solution/suspension is dispersed as droplets in an aqueous solution of (e.g., the hydrochloride salt of) a suitable water soluble amine. At the apparent interface of the polymer droplets and amine solution, a salt exchange reaction takes place to result in the formation of a very poorly soluble salt (formed between the amine and polymer) which precipitates to form more or less spherical beads or capsules in which immunogenic composition is captured. The resulting suspension of microcapsules containing encased immunogenic composition is collected.

The anionic polymer and reactant amine are chosen from groups which, on reaction with one another, will rapidly form a poorly soluble precipitate and so encase the droplets before the polymer in the droplets diffuses sufficiently to distort appreciably the shape of the droplet or to lower the polymeric reactant concentration below that required to form a film. Thus, it is not necessary to employ polymer solutions of high viscosity, but it is necessary that the amine be capable of rapid diffusion to, and reaction at, the pseudophase boundary defined by the polymer droplet. The viscosity of the polymer solution may be as low as 2.5 to 10 centipoise.

A convenient means of dispersing the polymer solution droplets (comprising a solution or suspension of immunogenic composition in the polymer solution) in the amine solution is to allow an aerosol of the polymer solution to fall onto/into the amine solution as it is stirred. Use of a Bernouli type nebulizer to generate the aerosol results in microcapsules with a relatively wide (Gaussian) distribution of particle sizes about the mean (with coefficients of variation approximating 10 to 20%). If narrower size distributions are desired, an acoustically pulsed droplet generator as described herein may be used to provide highly uniform microcapsules (with coefficients of variability of diameter approximating 5%).

In some instances, as when acid labile immunogenic compositions are to be administered orally, it may be desirable to coat the microcapsules with an enteric material to protect them from gastric acid. Suitable enteric coating materials include cellulose acetate phthalate and polyoxyethylene cross-linked polymethacrylic acid. The technology for providing enteric coatings for small particles, tablets and capsules is well known in the pharmaceutical industry.

The reactants employed in preparing the microcapsules from entirely aqueous solutions are available from a number of commercial vendors, but all have been purchased from Fisher Scientific Company, F. M. C. Corporation, Ruger Chemical Company, Sigma Chemical Company, and/or The Upjohn Company.

Rapid release of encapsulated materials is accomplished by adding to an aqueous suspension of the microcapsules a water soluble salt, either as solid or as a solution of such salt. In either case, the salt employed must be capable of reacting with the insoluble film to yield water soluble ionic products in a manner analogous to the reverse of the film forming reaction. It is evident that the film-forming reaction is a reversible reaction. Slow release of soluble small molecules is realized through their gradual diffusion through the microcapsular walls. Diffusion rates depend on the size and solubility of the diffusing species and on the thickness and density of the capsular wall. Thus, in addition to providing a rapid release when wanted, the encapsulation process may be employed to provide controlled slow release of soluble encapsulated materials.

Anionic polymers or macromolecules which have been shown to be useful as encapsulating reagents are drawn from the group of water soluble polymers with reactive carboxylate or sulfate groups consisting of alginic acids, alginic acids linked to fluorophores such as fluorescein isothiocyanate or rhodamine isothiocyanate, arabic acid, cellulose sulfate, carboxymethylcellulose, carrageenans, chondroitin sulfate, heparin, polyacrylic acid, polyoxyethylene crosslinked polyacrylic acid (e.g. Eudragit L-100$^R$, produced by Rohm Pharma) and polyvinylcarboxylic acid (e.g. Carbopol 934$^R$) In some preferred embodiments, the anionic polymer is selected from the group consisting of alginic acid (Fisher Scientific Co., Fairlawn, N.J.), polyacrylic acid (Aldrich Chemical Co., St. Louis, Mo.), cellulose sulfate (Aldrich Chemical Co., St. Louis, Mo.), Carbomer USP (Carbopol 934®, B. F. Goodrich, Cleveland, Ohio), carboxymethylcellulose USP (medium viscosity, Ruger Chemical Co. Inc., Irvington, N.J.), Heparin USP (The Upjohn Co., Kalamazoo, Mich.), and arabic acid (isolated according to the method described in U.S. Pat. No. 2,666,759 which is incorporated herein by reference), each of which is provided as a sodium salt. In some preferred embodiments, the anionic polymer is alginic acid provided as sodium alginate.

Cationic reactants useful in preparing microcapsules according to this invention are drawn from the group of mono-, di-, tri- and tetra-amino compounds which includes: arginine, decylamine, dodecylamine, ethylenediamine, piperazine, methylene blue, octadecylamine, triethylamine, triethyltetramine, and spermine. It is generally preferred that the anionic polymers be employed as their neutral salts with an alkali metal ion (e.g., sodium) and the basic reactants be employed in the form of their chloride or acetate salts. In some preferred embodiments, the amine is provided as a hydrochloride salt. In some preferred embodiments, the amine is selected from the group consisting of arginine (Sigma Chemical Co., St. Louis, Mo.), piperazine (Sigma Chemical Co., St. Louis, Mo.), ethylenediamine (Aldrich Chemical Co., St. Louis, Mo.), triethylamine (Aldrich Chemical Co., St. Louis, Mo.), triethylenetetraamine (Aldrich Chemical Co., St. Louis, Mo.), methylene blue (Fisher Scientific Co., Fairlawn, N.J.), and spermine each of which being provided as a hydrochloride salt, and octadecylamine (Sigma Chemical Co., St. Louis, Mo.) which is provided as an acetate. In some preferred embodiments, the amine is spermine provided as spermine hydrochloride.

Based on tests to date, among the materials which may be encapsulated according to this invention are the following: blue dextran, charcoal, fluorouracil, indomethacin, nicotinamide, phenol red, prednisolone, tetracycline, theophylline, larvacidal proteins of *Bacillus thuringiensis* (Bt) subsp. israelensis, and strains of viruses represented by the envelope and non-envelope viruses vaccinia and rotavirus, respectively.

Prior to formation of microcapsules with captured immunogenic compositions, the anionic polymers and amines are tested individually to determine their effect on immunogenicity of immunogenic composition.

In order to determine the effect of anionic polymers and amines on infectivity and immunogenicity, one having ordinary skill in the art can perform routine assays using readily available starting materials. For example, the ability of a selected immunogenic peptide or protein to invoke an immune response in the presence and absence of various concentrations of the component being evaluated may be determined to ascertain the effect the component has on the immunogenicity of the molecule. Likewise, the ability of a selected infectious agent to infect cells or an animal may be tested in the presence and absence of various concentrations of the component being evaluated to determine the effect the component has on infectivity. In the case of rotavirus, a rotavirus stock can be combined with the aqueous sodium salt of an anionic polymer or the aqueous salt of the amine or a control such as saline. The effect of the component on the rotavirus infectivity is determined by standard plaque assay.

Since in some embodiments it is preferred that the microencapsulated vaccine to be effective when administered orally, the anionic polymers and amines which do not inactivate the immunogenic composition are tested in combination to determine their capacity to form microcapsules that resist breakdown in simulated gastric acid.

The aqueous sodium salt of anionic polymer, preferably 1 ml, is added dropwise to aqueous amine hydrochloride (or acetate), preferably 1 ml, to determine the capacity to form an interfacial precipitate. Combinations which generate solid material are used to make microcapsules. Microcapsules are formed by dispersion of the sodium salt of anionic polymer as droplets approximately 5 μm in size into an aqueous solution of the amine salt in a manner analogous to that described for preparing calcium alginate microcapsules in U.S. Pat. No. 4,744,933, which is incorporated herein by reference. Short-term stability of microcapsules is tested by observation at room temperature for 5 days in aqueous solution. Microcapsules stable at room temperature are treated with simulated gastric acid (pH 1.2) at 37° C. for 2 hours.

The combinations of anionic polymers and amines which do not inactivate the immunogenic compositions and which provide stable microcapsules are then used to form microencapsulated vaccines. The immunogenic composition is first combined with the anionic polymer. The polymer/virus mixture is then dispersed as droplets into amine.

Further examples of human and veterinary vaccines and strains of rotavirus which can be encapsulated in accordance with the present invention are listed below.

1. Human Vaccines
Diphtheria toxoid
Pertussis toxoid
Tetanus toxoid
Hepatitis B surface antigen
Respiratory syncytial virus
Adenovirus
Parainfluenza virus
Canaraypox recombinants
Hepatitis A virus
Influenza virus, live or inactivated
Yellow fever virus
Live attenuated poliovirus
Rabies virus
Inactivated poliovirus
Cholera
Hemophilus Influenza type B
Yersinia pestis (plague)
Neisseria meningitidis
Salmonella typhi (typhoid)
Measles
BCG
Mumps
*Streptococcus pneumoniae*
Rubella
Varicella
Rotavirus
Human immunodeficiency virus
Herpes simplex virus
Cytomegalovirus
2. Veterinary Vaccines Cattle
Infectious bovine rhinotracheitis
Parainfluenza type 3
Bovine diarrhea virus
Bovine respiratory syncytial virus
Rotavirus
Coronavirus
Rabies
Haemophilus/Pasteurella species
Leptospira
Clostridia species
Tetanus toxoid Dogs Canine distemper/measles
Canine hepatitis
Parvovirus
Coronavirus
Rabies
*Borrelia burgdorferi*
Leptospira

Cats

Feline rhinotracheitis virus
Feline calicivirus
Panleukopenia virus
Feline leukemia virus
Feline infectious peritonitis virus
Rabies

Swine

Transmissible gastroenteritis
Rotavirus
Parvovirus
Pseudorabies
Pasteurella
Erysipelas
Leptospira sp.
Haemophilus sp.
Bordetella
Tetanus toxoid

Horses

Equine encephalomyelitis
Equine influenza
Equine rhincpneumonitis
Tetanus toxoid
Rabies 3. Rotavirus Strains Bovine WC3
HCR3a
Bovine WC3, modified with Human vp4 W179
Bovine WC3, modified with Human W178-8
Bovine WC3, modified with Human W179-9 or SC2-9
Bovine WC3, modified with Human W179-9 and -4
Bovine WC3, modified with Human vp4 DS1
Bovine WC3, modified with Human Bricout B-9
Bovine WC3, modified with Human vp4 Bricout A
HCR3a, modified with Human W179-9
Rhesus rotavirus RRV
RRV modified with Human Wa-9
RRV modified with Human DS1-9
RRV modified with Human P-9
RRV modified with Human ST3-9

Two types of virus, a strain of vaccinia virus, identified as VVUKvp7, and two strains of rotavirus, identified as WC3 and RRV have been successfully captured, sustained and later released from the microcapsules of the present invention. These two types of virus represent the two major categories of virus, envelope and non-envelope. Non-enveloped viruses, such as rotavirus, poliovirus, adenovirus, are much less susceptible to drying agents, detergents and surface cleansing agents than are enveloped viruses. As a result non-enveloped, but not enveloped, viruses survive well in sewage and on environmental surfaces. Enveloped viruses, due to their surface lipid bilayer, are not as hearty as non-enveloped viruses, and are susceptible to breakdown by contact with the agents listed above. Vaccinia virus was chosen as an encapsulation candidate because of its use as a recombinant vector into which DNA encoding immunogenic peptides and proteins may be relatively readily inserted. Strains of rotavirus were chosen for trial because rotavirus is known to cause severe and sometimes fatal diarrhea in human and other infants.

Microcapsules according to the present invention may be made with the apparatus described herein which allows preparation of microcapsules of extremely narrow size distribution at selectable median sizes. This is of importance in making microcapsules intended for injection or for uptake through the gut-associated lymphatic tissues (a subset of which are often referred to as Peyer's patches) or the bronchus-associated lymphatic tissue of the respiratory system. Microcapsules intended for intravenous injection must necessarily be less than about 5 microns in diameter, small enough to pass through capillary beds. For administration by inhalation, particles must be in the respirable size range, less than about 5 microns, and, to reach deep alveolar sites, it is preferred that particles be in the size range below 2 microns. The tissues of Peyer's patches are highly discriminatory in the size of particle which they will engulf and select only particles less than 10 and preferably about 5 microns in size. This device can produce populations of microcapsules of various sizes, with standard deviation from the mean of less than 0.25 micron in the range near the mean volume diameter of 5 microns.

The vaccines of the invention may be administered by a variety of routes including, for example, intraocular, intranasal, buccal, oral, inhalation, rectal, subcutaneous, intramuscular, intra-arterial, intravenous, and intraperitoneal. The vaccines of the invention may be delivered parenterally. Examples of such vaccines have been shown to enhance immunogenicity in laboratory mice several hundred- to thousand-fold compared to unencapsulated virus. The system works well with both purified virus and viral tissue culture suspensions so that laborious and expensive separation of viral particles is not required.

Microcapsule Forming Reactions:

In accordance with the present invention, one of two types of reactions can be employed to form the microcapsules in aqueous media. These are acid-base reactions and salt exchange reactions.

Acid-base Reaction:

Several water soluble acidic polymers will react in aqueous solution with low molecular weight water soluble mono- or oligo-amines to form poorly water soluble salts which may precipitate. The group of water soluble acidic polymers which participate in this reaction includes arabic acid, cellulose sulfate, chondroitin sulfate, heparin, and fluorescent derivatives of the above acidic polymers. The group of amines which yield poorly water soluble salts in this reaction includes decylamine, dodecylamine, ethylenediamine, hexadecylamine, methylene blue, octadecylamine, piperazine, spermine, tetradecylamine, triethylamine and triethylenetetramine.

Salt Exchange Reaction:

A similar reaction occurs with formation of poorly water soluble salts if the acidic polymers described above or certain relatively poorly water soluble acidic polymers are employed as solutions of their respective neutral salts (e.g., with sodium or ammonium ion) and the amines described above are dissolved as their water soluble salts (e.g., hydrochloride, acetate). The similar reaction may be considered a salt exchange reaction in which one of the products (e.g., sodium chloride or sodium acetate) is soluble and the amine-polymer salt is poorly soluble. The group of acidic polymers useful as their water soluble salts in the salt-exchange reaction includes those polymers named above and also the following acidic polymers in the form of their sodium or other water soluble salts: alginic acid and fluorescent derivatives, e.g. fluorescein isothiocyanate and rhodamine isothiocyanate, derivatives of alginic and other acids, carboxymethylcellulose, Eudragit L-100$^R$ (polyoxyethylene cross-linked polyacrylic acid), polyacrylic acid, polyvinylacrylic acid and fluorescent derivatives of these polymers. This larger group of acidic polymers will all react as their sodium or other water soluble salt with at least one of the members of the group of amines in the form of their hydrochloride or acetate salts to form poorly water soluble amine-polymer salts in the salt exchange reaction. However, not all combinations that form poorly soluble salts will form microcapsules in accordance with this invention. See the test described below and compare Tables 1 and 2 below.

As used herein, the terms "anionic polymer", "polymer strand" and "anionic polymer solution" are meant to refer to polymers which participate in forming the amine-polymer salt. References to concurrently formed water soluble products of the exchange reaction (e.g., sodium chloride or sodium acetate) are not expressly referred to herein unless there is specific need to refer to these water soluble products.

Thus, the group of anionic polymers that can be used as microcapsule forming agents in accordance with this invention consists of polymeric substances with carboxylate acidic functional groups (alginic, arabic, carboxymethylcellulose, Eudragit L-100, polyacrylic acid and polyvinylcarboxylic acid), sulfate acidic groups (carrageenans, cellulose sulfate, chondroitin sulfate, heparin), linear or branched polyalkylene backbones (polyacrylic acid, poly-vinylcarboxylic acid), linear carbohydrate backbones (alginic acid, cellulose sulfate, chondroitin sulfate, heparin) and branched carbohydrate backbones (arabic acid).

In the microcapsules of the present invention, the anionic polymer constitutes the major structural component of the microcapsular walls. Typically, the polymer is chosen to provide a desired range of spacing between nearest neighbor anionic groups. Thus, in their extended forms above the theta temperatures of the polymers, the interanionic distances approximate the equivalent of 2 methylene groups in poly-acrylic acid, 6 in alginic acid, cellulose sulfate, chondroitin sulfate, and heparin, 10 in carboxymethylcellulose and between 20 and 30 in highly branched arabic acid. This allows one to selectively form capsule walls having different porosities. See T. J. Speaker and L. Lesko, U.S. Pat. No. 3,959,457, Microparticulate material and method of making such material, May 25, 1976, column 5, lines 6 through 20.

Because all the anionic polymers used in the present invention have average molecular weights well above 10 kD, they are multivalent and can react with the amines in a wide range of stoichiometries. In practice it has been found that the preferred range of stoichiometries of amine to anionic polymer repeat unit is about 0.2 to about 0.6. In other words, about 2 to 6 amine molecules are available to combine with each 10 anionic group on the polymers, to form salts of the polymer. Further, because several of the amines are also multivalent, the reacting species can, in theory, form complex networks in which the amines serve to crosslink anionic polymer strands. The precipitates, which form essentially instantaneously when solutions of anionic polymers and amines are stirred together, tend to be amorphous, cohesive, adhesive and often filamentous. However, not all combinations of anionic polymer and amine yield poorly soluble amine-polymer salt. Table 1 below lists two groups of reactive species tested to date and indicates the combinations with which applicants have been successful in forming precipitates, when these combinations were allowed to react. The anionic polymers and amines are listed in order of increasing approximate equivalent weights (shown in parentheses) of the amines and polymer repeating units.

TABLE 1

Amine/Polymer Combinations Which Form Insoluble Salts

| Amines | | p-acrylic acid (74) | p-vinylcarboxylic acid (86) | alginic acid (176) | Eudragit L-100 (185) | cellulose sulfate (260) | carboxymethylcellulose (295) | heparin (480) | chondroitin sulfate (480) | cellulose acetate phthalate (563) | arabic (1000) |
|---|---|---|---|---|---|---|---|---|---|---|---|
| ethylenediamine | (30) | + | + | 0 | 0 | + | 0 | 0 | 0 | + | 0 |
| triethylenetetramine | (37) | + | + | + | 0 | + | 0 | + | 0 | + | 0 |
| piperazine | (43) | 0 | 0 | + | 0 | 0 | 0 | 0 | 0 | 0 | 0 |
| spermine | (51) | + | + | + | + | + | + | + | + | + | 0 |
| arginine | (87) | 0 | + | 0 | 0 | 0 | 0 | 0 | 0 | + | 0 |
| triethylamine | (95) | 0 | + | 0 | 0 | 0 | 0 | 0 | 0 | + | 0 |
| decylamine | (156) | + | + | + | + | + | + | + | + | + | + |
| dodecylamine | (170) | + | + | + | + | + | + | + | + | + | + |
| tetradecylamine | (184) | + | + | + | + | + | + | + | + | + | + |
| methylene blue | (187) | 0 | + | + | 0 | + | 0 | 0 | 0 | + | 0 |
| hexadecylamine | (198) | + | + | + | + | + | + | + | + | + | + |
| octadecylamine | (212) | + | + | + | + | + | + | + | + | + | + |

A plus mark (+) indicates formation of a precipitate when reactants are combined. a zero (0) indicates no precipitate forms.

Although the majority of the combinations of anionic polymer and amine will react to form a poorly water soluble amine polymer salt, a smaller subset of this set appears to be capable of forming microcapsules, at least under the conditions tested to date. Thus, the simple ability to form a water insoluble amine polymer salt does not in itself provide definitive identification of microcapsule wall forming components, at least under the conditions tested to date.

To determine whether a selected amine/polymer pair will form capsules and microcapsules, the following procedure is useful. Prepare separate aqueous solutions of the amine and polymer, containing about 1% w/v of the acid form of the polymer and an approximately stoichiometrically equivalent amount of amine, in equal volumes of water. Alternatively, if the polymer or amine are not soluble to such an extent, prepare separate solutions of water soluble salts of the amine (e.g., hydrochloride or acetate) and of the polymer (e.g., sodium or ammonium). To an approximately 5 milliliter volume of the amine solution add successive 20 to 25 microliter volumes of the polymer solution, delivering the polymer solution dropwise from a height of about 1 centimeter. Visually observe the two solutions as the one is added to the other. Note whether the droplets of polymer solution merge with the amine solution and the system becomes homogeneous or whether a pellicle forms about the polymer solution droplets and keeps them as physically distinct and mechanically separate entities.

If the added droplets form such a pellicle and do not blend with the amine solution to make a homogeneous solution, it is probable the reactant pair can be used to make microcapsules. To test this probability more closely, it is necessary to repeat the experiment using polymer droplets and amine solutions prepared over a range of concentrations to establish optimal reactant concentrations.

If either the amine or acid form of the polymer is inadequately soluble to conduct the test as described above, the salt forms of the reactant pair may be used together in their place.

Table 2 indicates which amine polymer salts have effectively formed stable microcapsules, under conditions tested to date.

TABLE 2

Amine/Polymer Combinations Which Form Stable Microcapsules

| Amines | | p-acrylic acid (74) | p-vinylcarboxylic acid (86) | alginic acid (176) | Eudragit L-100 (185) | cellulose sulfate (260) | carboxymethylcellulose (295) | heparin (480) | chondroitin sulfate (480) | cellulose acetate phthalate (563) | arabic (1000) |
|---|---|---|---|---|---|---|---|---|---|---|---|
| ethylenediamine | (30) | + | + | 0 | 0 | + | 0 | 0 | 0 | 0 | 0 |
| triethylenetetramine | (37) | + | + | + | 0 | + | 0 | 0 | 0 | 0 | 0 |
| piperazine | (43) | 0 | 0 | + | 0 | 0 | 0 | 0 | 0 | 0 | 0 |
| spermine | (51) | + | + | + | + | + | + | + | + | 0 | 0 |
| arginine | (87) | 0 | + | 0 | 0 | 0 | 0 | 0 | 0 | 0 | 0 |
| triethylamine | (95) | + | 0 | 0 | 0 | 0 | 0 | 0 | 0 | 0 | 0 |
| decylamine | (156) | + | + | + | + | + | + | + | + | 0 | + |
| dodecylamine | (170) | + | + | + | + | + | + | + | + | 0 | + |
| tetradecylamine | (184) | + | + | + | + | + | + | + | + | 0 | + |
| methylene blue | (187) | 0 | + | + | 0 | + | 0 | 0 | 0 | 0 | 0 |
| hexadecylamine | (198) | + | + | + | + | + | + | + | + | 0 | + |
| octadecylamine | (212) | + | + | + | + | + | + | + | + | 0 | + |

A plus mark (+) indicates the reactants will form microcapsules, a zero indicates they do not.

The ability of a combination of aqueous solutions of amine and polymer to form a stable microcapsular configuration requires first that the reactants be water soluble and oppositely charged in order that they may combine to form a poorly soluble salt. Importantly, the anionic polymer strands in solution must not rapidly diffuse compared to the ability of the amine molecules (ions) to diffuse. Further, it is preferred that the droplets of anionic polymer solution be introduced into the amine solution in such a manner that the polymer droplets do not become extensively distorted or very rapidly mixed with the bulk of the amine solution. These several requirements are relatively easily met. The basis for these requirements may be understood in terms of the steps in the process described in greater detail below.

At the start of the microcapsule making process, the aqueous solutions of anionic polymer and of the amine are mechanically (i.e., physically) separated phases. At room temperature, the water molecules of the anionic polymer solution are expected to have high (0.9+) thermodynamic activity coefficients (excluding the contribution of water) and to diffuse far more rapidly than do the polymer molecules. The polymer strands (molecular weights above 10 kD, 100,000 amu) are of colloidal size and can be expected to behave as do other colloidal particles. In particular, it is expected that a colloidal solution of anionic polymer will tend to structural inhomogeneity with development of microregions of relatively high colloidal polymer concentration and others void of polymer. This behavior of colloidal polymers has recently been shown by Ito et al. (1994) *Science* 263:66–68; with time lapse confocal laser micrographs. The micrographs show such tendency toward inhomogeneity and void structure. Ito et al. discuss this behavior in terms of ionic polymers such as those employed in this invention (e.g., sodium polyacrylate). By contrast, amine reactants (molecular weights less than 400) are thermodynamically far more active than are the anionic polymer strands, diffuse far more rapidly than do the polymer strands (but more slowly than do water molecules), and are understood to be homogeneously distributed throughout their solutions.

When a droplet of anionic polymer solution is introduced into a bulk volume of amine solution it is expected that the previously separate aqueous phases will essentially instantaneously combine to form a single continuous aqueous phase with no discernable phase boundary for the previously separate aqueous components. On the other hand, the low diffusion coefficients of the anionic polymers (typically less than $7 \times 10^{-7}$ cm$^2$/sec for colloidal polymers in the mass range near 10 kD) limit movement of polymer molecules from their initial positions relative to the remainder of the polymer solution droplet and allow time for a multiplicity of amine molecules (ions), moving nearly as rapidly as water molecules, to come into proximity with the polymers, to be electrostatically attracted to them, and to form salts with anionic groups of the polymers. Thus, the relative immobility of the polymer molecules during reaction with numerous amine units allows precipitation of a shell which conforms to the approximate initial positions of the polymer strands and retains the shape of the droplet.

The development of this shell around a droplet may be easily observed macroscopically by carefully adding an approximately 20 microliter approximately spherical droplet of aqueous 1% w/v sodium carboxymethylcellulose solution to an approximately 1% w/v aqueous solution of decylamine hydrochloride. Within a small fraction of a second, a barely discernable spherical pellicle forms around the added droplet and, during a few more seconds, the pellicle becomes increasingly thicker and more opalescent. The resulting microcapsule can be retrieved with a pasteur pipette or collected on fine netting. It should be noted that, if such a polymer droplet is delivered to the amine solution from a height of several centimeters, it is highly probable that the droplet may be distorted to form an oblate spheroid or biconcave disk-like structure which similarly gradually becomes thicker and more opalescent of shell. If the amine solution is stirred or rapidly flowing, added droplets tend to form prolate spheroids or filamentous particles which similarly thicken. If the droplets of polymer solution are smaller, they may be dispersed onto or into the amine solution from greater heights or onto/into flowing amine solution with less distortion. In practice, droplets of approximately 5 to 7 micron diameter-may be applied from a height of 5 centimeters to the surface of an amine solution flowing at linear velocity of about 1 centimeter per second and still produce essentially spherical microcapsules.

While it is perhaps too simple to describe the process by which pellicles surrounding polymer droplets form and thicken to make microcapsules in terms only of diffusional processes, such a description conveys a fairly accurate sense of what happens. A more detailed understanding may be derived through the description of the mechanism and dynamics of ion transport across a liquid-liquid interface. I. Benjamin (Science 261: 1558–1560, 1993) has shown that, although the time averaged water-dichloroethane interface is "molecularly sharp", over short time intervals, thermal fluctuations induce formation of capillary interdigitations of each liquid phase with the other. These capillary "fingers" allow ion transfer from one phase to another even though the bulk phases are clearly separate. It is to be expected that similar capillary intrusions of an amine bearing part of the aqueous phase into polymer bearing aqueous phase might similarly provide a mechanism by which the ions of the amine polymer salt might interact to develop a film or pellicle without grossly disturbing the integrity of the polymer droplet.

In effect, then, the ability of the reactant solutions to form discrete microcapsules depends at least in part on the relative immobility of polymer strands in aqueous media and the relatively much greater mobility of amine molecules (ions), and perhaps also in part on the brief thermally induced fluctuation of the apparent interfacial boundary between amine and polymer solutions. It does not require high viscosity solutions, but rather one species of slow diffusing reactant. This interpretation of the mechanism of microcapsule formation is quite at odds with the constraints on microcapsule formation put forth in other entirely aqueous encapsulation systems.

The reaction leading to formation of amine polymer salt precipitates may be seen to be a simple salt exchange and as such has the characteristics of a reversible reaction. That this is so is demonstrable by adding an excess of the soluble salt formed in the reaction, or a concentrated solution of it (e.g., sodium chloride or sodium acetate), to a suspension of microcapsules. Raising the concentration of sodium chloride in the aqueous medium surrounding a population of microcapsules to about 4% w/v generally results in their rapid dissolution. However, treatment with sodium chloride or another electrolyte capable of yielding soluble polymer and amine salts (e.g., sodium phosphate to make a 4% w/v solution) may not completely disrupt microcapsules made with very poorly soluble amines (e.g., hexadecylamine, octadecylamine), and, to disrupt such microcapsules, e.g. for analytical purposes, it is useful to add a solvent that is able to deplete the aqueous concentration of amine (e.g., cyclohexane).

A presently preferred method for forming the microcapsules of the invention is to employ an acoustical droplet forming device that has been developed for this purpose.

This device produces a stream of uniform fine droplets of anionic polymer solution and direct them onto and through a constantly renewed surface of the cationic reactant solution so that newly arriving droplets do not impinge on earlier delivered droplets. The device thereby (1) reduces the tendency to form microcapsule agglomerates and (2) provides a means to produce large populations of microcapsules with a very narrow size distribution range. The machine operates by sonically pulsing a downward flowing vertical stream of polymer solution just before it emerges from a narrow orifice so that the sound wave propagating through the liquid stream initiates a series of constrictions in the stream which then, under the influence of the surface tension of the liquid, causes the stream to break up into a train of uniform droplets. The droplet train is directed coaxially into a narrow cylindrical tube which is supplied through a side opening (or its topologic equivalent) with a continuous flow of the cationic reactant. Thus, each newly arriving polymer droplet encounters a fresh surface of cationic reactant and has minimal opportunity to strike and coalesce with another polymer droplet before it begins to form its own capsular wall and exits the lower end of the tube.

The major components of the acoustic device for preparation of microcapsules may perhaps be best described in terms of its functional sequence as it brings two liquid streams together to form microcapsules. In this device, aqueous solutions of anionic polymer and amine are stored in separate reservoirs and pumped through separate transfer lines. The amine solution is fed to and enters the stem of a modified T-tube which serves as the primary reaction vessel. The T-tube is mounted so that the cylindrical axis of the bar of the T is oriented vertically. Amine solution entering the stem of the T-tube flows horizontally for a few millimeters before it flows by gravity out the lower half of the T-tube bar. (In practice, it has been useful to employ not a simple T-tube but rather one of the sort often referred to in clinical chemical laboratories as a "cactus tube". A cactus tube has the general shape of the lower case letter h and, in this application, the tube is positioned so that the h shape is upside down. The straight part of the cactus tube is about 2 cm long and has an internal diameter of about 2 mm.) Amine solution flowing from the T-tube may be returned to the reservoir and recirculated.

The polymer solution is pumped through a membrane filter (of 8 micron or finer retentiveness), then through a glass capillary, the distal end of which is constricted to a nominal diameter of 20 to 25 microns, and emerges in the form of a fine continuous liquid jet. (The constricted capillary is readily fabricated from a volumetric 25, 50 or 100 microliter glass capillary tube of a type generally available from laboratory supply houses, e.g., A. H. Thomas Co. The constriction is preferably such that the jet of polymer solution emerges with a velocity in the range between 4 and 5 meters per second when the polymer solution is pumped at 1 to 2 milliliters per minute, but flow rates and velocities outside these ranges may, of course, be employed.)

The capillary is aligned in a shallow V-shaped groove in a metal block and tightly held by compression springs against the axially vibrating end of an acoustic transducer (e.g., of a laboratory ultrasonic probe operated at a nominal energy output of 40 watts) so that acoustic energy is transferred through the wall of the capillary to the flowing polymer solution, causing the jet of polymer solution to break up into a train of droplets of uniform size.

The transducer-capillary-compression block assembly is positioned so that the emerging train of polymer solution droplets passes through air for about 3 cm and is directed axially into the upper end of the T-tube bar to impinge on the amine solution entering from the side (stem) of the T-tube. The polymer solution droplets react with the amine solution to form microcapsules that flow with the amine solution out the lower end of the T-tube bar.

Even in the absence of sonic stimulation, the jet of polymer solution which emerges from the capillary constriction, as described above, would normally spontaneously break up into a train of droplets of varying size as a result of varying natural instabilities of the fluid stream and of the atmosphere into which the jet emerges, the so-called Rayleigh disruption of a liquid jet. However, it is desirable that droplets of uniform size be produced in order to make microcapsules of uniform size. It is for that reason that, in accordance with the preferred embodiment of this invention, that droplets of uniform size are produced by periodically sonically disturbing the liquid stream to initiate a train of sufficiently strong compression (sound) waves along the axis of the jet. The train of sound waves moves through the liquid medium and away from the orifice far more rapidly than the liquid itself. (The jet emerges at a velocity of 4 to 5 meters per second.) Propagation of the wave train along the length of the jet establishes an interference pattern of increasing constructive amplitude at successive nodes along the path of the jet. At some distance from the orifice, the amplitude of the surface wave becomes greater than the surface tension of the liquid, and droplets of polymer solution form at the sonicator frequency. The generation of a train of droplets of uniform size in this manner is reported in some detail by P. J. Galley and G. M. Hieftje, Applied Spectroscopy 45:1460–1463 (1992).

To illustrate the foregoing method and apparatus, reference is made to the accompanying FIG. 1, in which is shown "h" shaped tubular member 10, including a side-leg entry segment 14 and a vertical intersecting segment 12, through which the amine solution 16 is pumped downwardly at the upper end of tube segment 14 so that it enters upright segment 12 and is diverted at the intersection of segment 14 and segment 12 into a downwardly flowing portion from which it exits at the bottom end of tubular segment 12. Above the intersection of segments of 14 and 12, the polymer solution 22 is introduced through a capillary member 18, the bottom end of which is spaced a predetermined distance (about 3 centimeters in the exemplary description above) above the intersection of segments of 14 and 12, at which the flow of the amine solution is diverted downwardly, so that drop-wise disposed portions of polymer solution 22 are combined with the downwardly flowing amine solution at that point.

As described above, to enhance the uniformity of the drop-wise downwardly flowing portions 22 of polymer solution, capillary tube 18 is rigidly held in a metal block 24, with a V-groove holding slot (not shown in the figure) and acoustically stimulated intermittently. For that purpose, an acoustic probe 20 is in contact with capillary tube 18 near the lower end thereof.

One may estimate the numbers of individual droplets produced per unit time from the frequency of the sonicator. In most instances, a sonicator with a frequency of 20 kHz was employed. The estimate of the number of droplets formed may be slightly in error due to instances in which successive droplets may impinge on one another and coalesce or adhere to one another to form aggregated microcapsules. In practice, far less than 1% of the droplets occur as fused or coalesced forms. Assuming all droplets are formed separately, one may calculate the size of individual droplets from a knowledge of polymer flow rate. At a nominal anionic polymer Flow rate of 1 milliliter per minute, the volume of individual droplets is 0.05 microliters (cubic millimeters), corresponding to a spherical droplet diameter of 4.57 microns. The diameter of microcapsules formed at flow rates near 1 milliliter per minute and acoustic frequencies of 20 kHz is approximately 5 microns as estimated from volume diameter sizing (Coulter principle).

Alternatively, droplets of the polymer solution of essentially any size may be introduced into the cationic reactant solution (e.g., by spraying, or by dropwise dispensing from a pipette) to form microcapsules. In many applications it is desirable that the microcapsules formed be of highly uniform size and thus some means of inducing this uniformity, such as the acoustic method described above, is preferred. Such applications include delivery to the lymphatic tissues of the intestine, often referred to as Peyer's patches. The M cells of Peyer's patches preferentially reject particles larger than about 10 microns but engulf particles in the size range below about 10 microns and transfer them to other lymphatic cells.

In general, the microcapsules of the present invention may range in size from 0.1 to 2,000 microns. A preferred size range, useful for general oral administration, is from 500 to 1,000 microns. In some embodiments, the range is from 100 to 200 microns. In other embodiments, such as in the administration of substances intended for delivery to Peyer's patches in the lymphatic tissue of the intestine, a particularly preferred size range is from 1 to 10 microns.

Depending in part on the degree to which manufacturing fluid is removed and in part on the nature of the core solute, the aqueous core microcapsules may be collected as a free-flowing suspension, a viscid flowable concentrate, a paste, a is friable flake or, with further treatment, as a lyocake. Lyophilization is particularly desired to provide stable microcapsules with highly water soluble core materials.

Once encapsulated, core materials, such as rotavirus, are protected from the environment, but may be slowly released from the microcapsules by suspending the capsules in an aqueous medium into which the core materials can actively diffuse through the semi-permeable microcapsule walls. In general, if the nature of the wall-forming reactants is maintained constant, highly water-soluble core materials are observed to be released more rapidly than are poorly water-soluble core materials and, in general, substances of low molecular weight are released more rapidly than are those of higher molecular weight. In some embodiments, conversion of the microcapsules to lyocakes and resuspension in aqueous media is preferred.

Vaccines according to the invention comprise at least one microencapsulated immunogenic composition, e.g., rotavirus, and a pharmaceutically acceptable carrier or diluent. Optionally, the vaccine may comprise additional components including microencapsulated and non-microencapsulated immunogenic compositions and/or adjuvants.

Vaccines of the present invention may be formulated following accepted convention using buffers, stabilizers, preservative, solubilizers and compositions used to facilitate sustained release. Generally, additives for isotonicity can include sodium chloride, dextrose, mannitol, sorbitol and lactose. Stabilizers include gelatin and albumin. Adjuvants may be employed. Examples of adjuvants include RIBI (Ribi Inc.), Alum, Freund's Complete, Freund's Incomplete, Block co polymer (CytRx, Atlanta Ga.), QS-21 (Cambridge Biotech Inc., Cambridge Mass.) and SAF-M (Chiron, Emeryville Calif.). Vaccines may be maintained in solution or, in some cases, particularly recombinant vaccines, lyophilized. Lyophilized vaccine may be stored conveniently and combined with sterile solution before administration.

The amount of microencapsulated immunogenic composition administered depends upon such factors as the nature of the immunogenic composition, the species, age, weight, and general physical characteristics of the animal being vaccinated, and by the composition of the vaccine. Determination of optimum dosage for each parameter may be made by routine methods. Generally, according to some embodiments of the present invention, vaccines contain between 0.05–5000 micrograms of immunogenic composition per milliliter of sterile solution, preferably 10–1000 micrograms. About 0.5–2 milliliter of protein-containing solution is administered. The amount of infectious agent administered depends upon such factors as the level of infectivity desired, the species, age, weight, and general physical characteristics of the animal being vaccinated, and by the composition of the vaccine. Determination of optimum dosage for each parameter may be made by routine methods.

Vaccines according to the invention may be administered by an appropriate route such as, for example, by oral, intranasal, intramuscular, intraperitoneal or subcutaneous administration. In some embodiments, oral administration is preferred. Subsequent to initial vaccination, mammals may be boosted by revaccination.

The utility of the microcapsules of the invention for delivery of various active agents is demonstrated in the following examples.

EXAMPLE 1

Placebo Microcapsules

Step 1: For convenience, anionic polymers were initially prepared as 1% w/v solutions in water and adjusted if necessary to pH values of 7.0+/−0.1 with dilute sodium hydroxide or sodium bicarbonate. Poorly water soluble anionic polymers such as acrylic acid and cellulose acetate phthalate were brought into solution as their sodium salts. Fresh polymer solutions were allowed to hydrate overnight before use, were stored at refrigerator temperature, and were allowed to equilibrate to room temperature before testing or use.

Step 2: Amine solutions were prepared as 1% w/v solutions in water and adjusted to pH 7.0+/−0.1 with the aid of dilute hydrochloric acid (or, in the case of some long chain aliphatic primary amines, acetic acid). Poorly soluble amines such as octadecylamine were warmed if necessary and brought into solution as their salts.

Step 3: The ability of amine and polymer combinations to form insoluble precipitates and useful microcapsules was assessed by adding approximately 50 microliter droplets of anionic polymer solution to approximately 5 milliliter volumes of amine solution in small test tubes. If the added anionic polymer solutions did not yield insoluble precipitates, the reactant pair was considered unlikely to merit further consideration. Combinations of reactants which did yield insoluble precipitates were carried into step 4 below.

Step 4: For each reactant pair selected for further study in step 3 above, a 5 milliliter volume of anionic polymer solution was diluted with an equal volume of water and nebulized onto 25 milliliters of magnetically stirred amine solution contained in a 10 cm petri dish (without cover) from a height of 10 cm. Nebulization was accomplished by pumping the anionic polymer solution at a rate of 1 milliliter per minute through an 18 gauge hypodermic needle and passing from a 12 gauge hypodermic needle a current of air at 4 liters per minute past the tip of the polymer delivery needle.

To provide a reproducible narrow cone of dispersal of the polymer solution, the tip of the 18 gauge needle was filed to a 75 degree angle and that of the 12 gauge needle to 90 degrees. The 18 gauge needle was mounted horizontally with the oval opening oriented upward toward the 12 gauge needle, which was positioned vertically. The tip of the air stream (12 gauge) needle was fixed in position 2 millimeters above the tip of the polymer delivery needle by spot welding the barrels of the needles to stainless steel cross braces so that the air stream blew across the polymer stream as it emerged from the modified 18 gauge needle. A series of trial experiments were required to optimize the nebulizer (e.g., the angle of the polymer delivery needle tip). For these trials, aqueous dye solution was used instead of water to dilute the polymer solution, and the colored polymer was sprayed onto 12 centimeter circles of filter paper.

The utility of an amine polymer combination in forming microcapsules was assessed by examining the reaction mixture during and after nebulizing to determine whether the mixture consisted of disperse particles capable of displaying a Tyndal effect, adhered to the glass surface of the petri dish, and/or appeared as roughly spheroidal particles when microscopically viewed at 100×magnification. The results are summarized in Table 2. Those reactant combinations which gave discernable spheroidal particles were further evaluated for stability and utility as encapsulants for a variety of active core materials as described herein.

Alternatively, to examining reactant pairs with the air-driven nebulizing device for their ability to form microcapsules, a limited number of amine polymer combinations were evaluated using the acoustic device described above.

EXAMPLE 2

A 10 mL volume of a 0.5% solution of sodium alginate in water was dispersed in the form of approximately 5 micron diameter droplets onto the gently stirred surface of 20 mL volume of a 0.05% solution of spermine (as the hydrochloride) over an approximately 10 minute interval. The mixture was centrifuged (2000 gravity minutes) and the supernatant was decanted from the resulting microcapsular pellet. When a small portion of the pellet was examined at 100×magnification it was seen to consist of numerous tiny spheroidal particles.

EXAMPLE 3

In order to examine the stability of the placebo microcapsules such as those described in Examples 1 and 2, stored in water for several days, toward artificial gastric fluid, and toward high electrolyte concentration, a suspension of spermine alginate microcapsules, prepared as described in Example 2, was resuspended in 20 milliliters of water and divided into four equal portions.

One portion was reserved as a control.

A second aliquot of a few microliters of the fresh suspension was withdrawn, and the remainder set aside stoppered at room temperature. On each of the following 4 days, the remainder of this portion was resuspended by vortexing and a few microliters were withdrawn. The microliter samples were promptly mounted on a microscope slide, examined, and photographed at 100×magnification. The developed is micrographs were compared to see if the individual particles changed in appearance or aggregated on standing.

A third aliquot was mixed with an equal volume of artificial gastric fluid and examined immediately and again after 2 hours incubation at 37 degrees centigrade to determine whether the microcapsules would lyse when exposed to an acidic environment like that of the stomach.

A 180 mg portion of solid sodium chloride was added to fourth aliquot and the mixture was vortexed until the sodium chloride dissolved. The portion to which sodium chloride had been added was examined visually and at 100× magnification to determine whether the added salt influenced the stability of the microcapsules.

Results:

Examination of the portion stored for 5 days did not show any appreciable change when examined visually or when the photomicrographs were compared. The portion treated with acid did not dissolve either immediately or on incubation for 2 hours, but the portion treated with approximately 4×normal osmolar sodium chloride clarified before all the salt had dissolved. No microcapsules were seen when the salt treated portion was examined microscopically. Spermine alginate microcapsules were judged to be unstable to concentrations of electrolyte several times higher than the normal osmolarity of human tissues.

EXAMPLE 4

It was of interest to examine the influence of stoichiometry of various combinations of amine and anionic polymer in terms of the yield of microcapsules formed. To this end a series of samples of microcapsules generated with the acoustic device described in herein with reference to FIG. 1 were prepared by reaction of serial dilutions of anionic polymer with a constant amine concentration, as follows.

Step 1: A solution of 1% w/v sodium alginate in water was prepared and, after hydrating for at least 24 hours, was filtered through an 8 micron filter.

Step 2: A 260 milliliter volume of 0.05% w/v spermine (as the hydrochloride) was prepared.

Step 3: A 10 milliliter volume of sodium alginate solution was diluted with an equal volume of water and, after mixing, 10 milliliters of the dilution were used with 42 milliliter volumes of spermine solution to prepare microcapsules with the acoustic device described above. The remaining sodium alginate dilution was reserved for use in step 4.

Step 4: The sodium alginate dilution from step 3 was diluted with another 10 milliliters of water and, after mixing, 10 milliliters of the new dilution was used with 42 milliliters of spermine solution to prepare microcapsules with the acoustic device described above. The remaining sodium alginate solution was reserved for use in step 5.

Step 5: The process described in step 4 above was successively repeated to generate a series of spermine alginate microcapsules from solutions of successively lower concentrations of sodium alginate.

Step 6: The successive batches of spermine alginate microcapsules prepared in steps 4 and 5 were. vortexed to mix them thoroughly, and the apparent absorbance of each suspension was immediately measured at 550 nanometers, a spectral region in which it had previously been determined the reactants themselves had no measurable absorbance. Aliquots of a few microliters of each suspension were mounted on microscope slides and photographed at 100× magnification. The remaining samples were stoppered, stored at room temperature, and re-examined and photographed after 50 hours.

| alginate % w/v concentration | millimoles alginate* | millimoles spermine | reactant* ratio | apparent 550 nm absorbance |
|---|---|---|---|---|
| 0.50 | 0.028 | 0.056 | 1:2 | 0.14 |
| 0.25 | 0.014 | 0.056 | 1:4 | 0.19 |
| 0.125 | 0.007 | 0.056 | 1:8 | 0.26 |
| 0.063 | 0.0035 | 0.056 | 1:16 | 0.31 |
| 0.032 | 0.0018 | 0.056 | 1:32 | 0.20 |
| 0.016 | 0.009 | 0.056 | 1:64 | 0.06 |

*alginate millimoles calculated in terms of alginate repeating unit

The absorbance measurements indicate the greatest density of spermine alginate microcapsules results from use of the reactants in the concentration ratio of one mole of alginate repeating unit to 16 moles of spermine.

EXAMPLE 5

It is well known that the ratio of reactants in the reaction mixture does not necessarily duplicate the ratio of reactants combined in the product of a chemical reaction. In some instances an excess of one reactant is required or desired to force the reaction toward improved yields of desired product. In this example, preferred stolchrometrio ratios of reactants were determined as follows.

A batch of spermine alginate microcapsules was prepared using the concentration of reactants which provided the highest density of microcapsule yield as described in Example 4, Step 6, above, and the product was repeatedly collected by centrifugation and resuspension in fresh water. The washed sample was air dried and submitted for combustion analysis by an external firm specializing in such work. The firm was directed to dry the samples to constant weight at temperatures below 50 degrees centigrade (to avoid forming anhydro derivatives of the carbohydrate derived polymer).

The combustion analysis showed the product to contain the equivalent of approximately 25% spermine (or about 1 spermine molecule for each 4 alginate repeating units). Thus, the reaction to form microcapsules is optimized at a high amine to anion reactant ratio, but not all the available amine can possibly react to form the amine polymer salt. It would appear that each of the amino groups in this polyfunctional amine reacts with one acidic alginate repeating unit.

EXAMPLE 6

A desired property of microcapsules prepared as described herein is that the microcapsules remain as stable, individual, particles and display little or no tendency to aggregate with time. To assess this quality, a series of microcapsule formulations of differing stoichiometries was examined at successive intervals after preparation.

The formulations prepared in Example 4 above were stored in teflon lined screw cap tubes in the temperature range between 21 and 25 degrees Centigrade. At approximately 2 month intervals over a period of 6 months, the samples were vortexed 3 times for approximately 30 seconds, and aliquots of a few microliters were examined at 100×magnification.

Formulations prepared from 0.50% and 0.25% alginate were extensively clumped at the end of the first 2 month interval and all later times. The sample made with 0.125% alginate was monodisperse at 2 months but slightly clumped at 4 and 6 months (aggregates of 10 to 20 particles each). The formulations prepared at the lowest concentrations tested, 0.06% and 0.03%, remained monodisperse after 6 months.

EXAMPLE 7

In order to determine some estimate of the range of core materials which might be effectively utilized in the entirely aqueous encapsulation system, a series of encapsulations were performed using two water soluble drugs, two water soluble adjuvant materials, two water insoluble solids, two types of virus and spermine alginate, spermine chondroitin sulfate, ethylenediamine cellulose sulfate, or octadecylamine carboxymethylcellulose as the wall forming materials.

EXAMPLE 7a

Step 1: A 15 mg sample of tetracycline base (Sigma Chemical Co.) was dissolved in 10 milliliters of aqueous 0.06% sodium aliginate solution and, using the acoustic device described above, this solution was combined with 20 milliliters of a 0.05% aqueous solution of spermine hydrochloride to form microcapsules containing tetracycline.

Step 2: The microcapsule suspension was centrifuged (5,000 gravity minutes) and, after decanting the supernatant, the pelleted microcapsules were washed 5 times by resuspension in enough water to make 5 milliliters, repelleting (by centrifuging), and decanting, in each instance retaining the decanted liquids. The final pellet was resuspended in enough water to make 10 milliliters and 500 milligrams of solid sodium chloride was added to it. The mixture was vortexed briefly to aid dissolution of the microcapsules and added salt. Approximately 1 microliter volumes of hydrochloric acid were added to the dissolved microcapsules and to each of the retained decanted liquids, and the absorbance of each solution was measured at 268 nanometers.

The supernatant liquids obtained after 3 washed showed no significant absorbance characteristic of tetracycline, but the absorbance of the solution of dissolved microcapsules at 268 nanometers indicated that more than half the initial amount of tetracycline was retained in the microcapsules during the repeated washings.

EXAMPLE 7b

Step 1: Fluorouracil (Sigma Chemical Co.) was substituted for tetracycline base and encapsulated as described in Step 1 of Example 7a above.

Step 2: The microcapsule suspension obtained in Step 1 above was treated as described in Step 2 of Example 7a above, except that absorbance measurements were made at 265 nanometers.

The supernatant liquids obtained after 3 washes showed no significant fluorouracil absorbance, but the absorbance at 265 nanometers of the solution of dissolved microcapsules indicated that more than half the initial amount of fluorouracil was retained in the microcapsules during the repeated washings.

EXAMPLE 7c

Step 1: A 100 mg sample of blue dextran (Sigma Chemical Co.) (average molecular weight 2,000,000) was substituted for tetracycline base and encapsulated as described in Step 1 of Example 7a above.

Step 2: The microcapsule suspension obtained in Step 1 above was treated as described in Step 2 of Example 7a above, except that absorbance measurements were made at 620 nanometers.

The supernatant liquids obtained after 3 washes showed no significant absorbance characteristic of blue dextran, but the absorbance at 620 nanometers after dissolving the microcapsules indicated that more than half the initial amount of blue dextran was retained in the microcapsules during the repeated washings.

EXAMPLE 7d

Step 1: A 100 milligram sample of bromphenol blue (Fisher Scientific Co.) was dissolved in 25 milliliters of a 0.1% solution of sodium carboxymethylcellulose (medium viscosity, Ruger Chemical Co.) and the resulting solution was slowly pumped (approximately 1 milliliter per minute) through a capillary drawn to a fine tip (0.1 millimeter o.d.). The emerging droplets were allowed to fall a distance of about 1 centimeter into a slowly stirred 0.1% aqueous solution of octadecylamine (Aldrich Chemical Co.) solubilized as the acetate at pH 7.0.

Step 2: The resulting approximately 1.5 millimeter diameter microcapsules were stirred for an additional hour and separated with the aid of fine netting. The microcapsules were washed with two 100 milliliter volumes of water. About half the microcapsules were stored wet and refrigerated until used. The other half of the microcapsules were lyophilized and stored dry until used.

Step 3: A few dozen of the lyophilized microcapsules were rehydrated in a few milliliters of water for an hour and were used in parallel with the wet stored microcapsules to test their sensitivity to pH. Dilutions of hydrochloric acid were made to provide solutions with pH values of 2, 3, and 4. To these hydrochloric acid solutions, a few rehydrated and a few wet stored microcapsules were added one at a time. The microcapsules were observed in order to determine whether they responded to the surrounding media by changing color in a manner consistent with the expected change of encapsulated bromphenol blue indicator from blue at pH 4 to yellow at pH 3.

The initially wrinkled lyophilized microcapsules assumed a spheroidal shape over an interval of about 20 minutes when added to water. Both the rehydrated and wet stored microcapsules remained blue when added to pH 4 medium but changed to yellow within a few minutes of being added to the pH 3 solution. The encapsulated bromphenol blue served as an indicator of the pH value of the interior of the microcapsule and did not diffuse out of it.

EXAMPLE 7e

Step 1: A 200 mg sample of finely ground charcoal was suspended in 25 milliliters of a 0.1% solution of sodium carboxymethylcellulose and encapsulated as described in Step 1 of Example 7d above.

Step 2: The resulting approximately 1.5 millimeter diameter microcapsules were stirred for an additional hour and separated with the aid of fine netting. The microcapsules were washed with two 100 milliliter volumes of water and stored wet at room temperature for 2 months. The charcoal-containing microcapsules were examined every 2 weeks to determine whether the microcapsules remained intact or lost any of the encapsulated solid.

The charcoal-containing microcapsules remained intact over the period of observation and there was no evidence of escape of the solid core material from the microcapsules during this period.

EXAMPLE 7f

Step 1: A 10 milligram sample of crystal toxin isolated from a strain of *Bacillus thuringiensis* subsp. israelensis (Ecogen, Inc.) was suspended in 25 milliliters of a 1% solution of sodium cellulose sulfate (Aldrich Chemical Co.) and delivered dropwise as described in Step 1 of Example 7e above to 50 milliliters of a 1% aqueous solution of ethylenediamine solubilized as the hydrochloride at pH 7.

Step 2: The resulting microcapsules containing crystal toxin were stirred for an additional hour and separated with the aid of fine netting. The microcapsules were washed with two 100 milliliter volumes of water, drained dry, and lyophilized. Residual ethylenediamine solution and both wash fluids were retained.

Step 3: 50 of the lyophilized microcapsules were rehydrated in a few milliliters of water for an hour, and the rehydration fluid was drained away and retained.

Step 4: The rehydrated microcapsules were lysed, and the crystal toxin dissolved by adding 10 milliliters of 1 Molar trisodium phosphate to them and diluting the mixture to 100 milliliters.

Step 5: The protein contents of the residual reaction fluid, both washes, the rehydration fluid, and the dissolved microcapsules were determined by measuring the absorbance of the protein-copper (I) complex with 4,4'-dicarboxy-2,2'-biquinoline at 562 nanometers.

Well over 90% of the initial amount of crystal toxin protein was retained in the microcapsules, with only a small portion lost during the microcapsule forming reaction.

EXAMPLE 7g

In order to demonstrate the utility of this invention for encapsulation of virus, three types of experiments were carried out with several sets of reagents, often with different lots of virus, but the intent and methodology of each trial within a type experiment were the same. These three type experiments were: 1) Preparation of placebo and virus-containing microcapsules, 2) Release of virus from microcapsules, and 3) Titration of placebo and virus microbeads.

Two types of virus were encapsulated: rotavirus strain WC-3 with a titre of $5.4. \times 10^6$ pfu/mL (plaque-forming units per milliliter) and a vaccinia virus strain VVUKvp7 with a titre $8.5 \times 10^6$ pfu/mL Step 1: A 5 mL sample of a 1.0% w/v neutral aqueous solution of anionic polymer (e.g sodium alginate) is diluted with 5 mL of water and mixed by vortexing. The diluted sample is transferred to a nebulizer, and microcapsules are prepared as described in Step 4 of Example 1 above by nebulizing the dilution onto a approximately 40 square centimeter surface of a magnetically stirred 25 mL volume of neutral 0.2 mM aqueous solution of amine hydrochloride (e.g. spermine hydrochloride).

Step 2: The nebulizer is rinsed with 1 mL of water, and the rinsing is similarly nebulized onto amine solution as in Step 1 above.

Step 3: The resulting microcapsule suspension is transferred to a calibrated centrifuge tube, the microcapsules are separated by centrifugation, and the total liquid and settled microcapsule volumes are measured.

Step 4: The microcapsules are stored refrigerated until ready for use, then redispersed by vortexing.

Step 5: Steps 1 through 4 above are repeated, substituting the 5 mL of viral suspension (e.g. rotavirus WC-3) for 5 mL of water in step 1 above.

Step 6a: The microcapsules are washed by pelleting at 1500 g×m (gravity×minutes), decanting, and resuspending in a volume of distilled water equal to one-fifth (⅕) the original volume. For placebo capsules only, a charge of virus suspension estimated to approximate the encapsulated virus is added to the resuspended capsules as detailed in Step 13. To rapidly disrupt placebo or virus microcapsules prepared from long chain alkylamines (e.g. octadecylamine as acetate), equal volumes of microcapsule suspension are mixed with aqueous 300 mOsmol (milliOsmoles) pH 7.0 phosphate buffer or fresh aqueous 0.5 M sodium bicarbonate and overlayed with an equal volume of cyclohexane. The mixture is vortexed briefly every minute for 5 minutes. Then the cyclohexane layer is aspirated. The virus, if any, will be in aqueous phase.

Step 6b: To rapidly disrupt placebo or virus microcapsules prepared from polyfunctional amines (e.g., spermine as hydrochloride), equal volumes of 1200 mOsmol sodium chloride and microcapsule suspension are mixed, or enough solid sodium chloride is added to the microcapsule suspension to make the resulting solution contain 4% sodium chloride.

Step 7: Monolayer cultures of green monkey kidney are prepared in multi-well (2.5 cm) tissue culture plates starting 72 hours before disrupting the microcapsules.

Step 8: Six serial 10-fold dilutions of stock viral suspension, which contains approximately $10^7$ plaque forming units per mL (pfu/mL), and, separately, of the supernatants from the microcapsule washes and the disrupted microcapsule suspension (of Step 6a) are prepared in AVN medium.

AVN medium is a mixture containing:
1. Commercially available Stoker's medium, which contains:
   sodium chloride,
   potassium chloride,
   sodium dihydrogen phosphate,
   dextrose,
   ferric nitrate,
   calcium chloride,
   magnesium sulfate,
   vitamins,
   amino acids,
   sodium bicarbonate,
   phenol red indicator,
   all dissolved in distilled water,
2. tryptose phosphate broth,
3. glutamine, and
4. a mixture of penicillin and streptomycin Step 9: The cells are washed twice with saline, discarding the washings.

Step 10: Successive adjacent wells are inoculated with 200 uL aliquots of successive viral dilutions and incubated for 30 minutes at 37 degrees.

Step 11: The cells are overlaid with 2.5 mL/well of a 1:1 mixture of minimal salts and agarose/trypsin. The overlaid cells are incubated for 72 hours at 37° C.

Step 12: The cells are stained with 1.5 mL/well of a 1:1 mixture of agarose and 2×Earl's balanced solution containing neutral red. The cells are incubated at 37° C. for 24 hours and plaques, if any, per well are counted. The cells are incubated for an additional 24 hours at 37° C. and new plaques, if any, per well are counted and the number of pfu in the original viral suspension is calculated.

Step 13: For placebo microcapsule titration, step 7 above is repeated. Then a known volume of stock viral suspension adequate to provide a viral concentration of about $10^5$ pfu/mL is added to a approximately 25 mL volume of placebo microcapsule suspension, and the suspension is mixed by vortexing.

Step 14: The suspension is centrifuged and the aqueous phase aspirated as completely as is practicable. Both the microcapsules and aspirate are saved.

Step 15: The microcapsules are resuspended in 10 volumes of water, again centrifuged and the aqueous phase is aspirated. Both the microcapsules and aspirate are saved.

Step 16: Step 15 is repeated.

Step 17: The microcapsule sample is divided into 2 equal portions and disrupted as described in Step 6a or 6b above.

Step 18: Steps 7 and 9 through 12 above are repeated, substituting in step 12 the successive aspirates, the remaining microcapsule suspension and the disrupted microcapsule preparation for the serial dilutions of viral suspension.

Step 19: To titrate microcapsules containing virus, steps 13 through 19 are repeated, substituting the viral microcapsule suspension for the placebo microcapsule suspension.

The foregoing sequence of steps for control, viral microcapsule and placebo (reagent blank) microcapsule titrations may be summarized as follows. In virology, a titration is a count of viral plaques in a cell culture.

| | step number | | |
|---|---|---|---|
| Description of Step | control culture | placebo u-caps | viral u-caps |
| Prepare Microcapsules | | | |
| mix polymer, make microcapsules | — | 1 | 5 |
| rinse system | — | 2 | 2 |
| centrifuge | — | 3 | 3 |
| store microcapsules | — | 4 | 4 |
| disrupt microcapsules | — | 6 | 6 |
| Count viral plagues in cell cultures | | | |
| grow monkey cell cultures | 7 | 7 | 7 |
| make dilutions of stock virus culture | 8 | — | — |
| wash monkey cell cultures | 9 | — | — |
| add stock virus culture to monkey cells | 10 | — | — |
| wash and incubate cells | 11 | — | — |
| count viral plagues in cell cultures | 12 | — | — |
| Use placebo microcapsules as reagent blank | | | |
| add dilutions of stock virus to placebo | — | 13 | — |
| centrifuge, separate phases | — | 14 | — |
| wash microcapsules by resuspending, centrifuging | — | 15 | — |
| again wash microcapsules | — | 16 | — |
| disrupt placebo microcapsules as in step 6 | — | 17 | — |
| step 18 encompasses the following procedures | | | |
| wash monkey cell cultures | — | 9 | — |
| add disrupted microcapsules, washes to monkey cells | — | 10 | — |
| wash and incubate cells | — | 11 | — |
| count viral plaques in cell cultures | — | 12 | — |
| Estimate virus content of viral microcapsules | | | |
| centrifuge, separate phases | — | — | 14 |
| wash microcapsules by resuspending, centrifuging | — | — | 15 |
| again wash microcapsules | — | — | 16 |
| disrupt viral microcapsules as in step 6 | — | — | 17 |
| step 18 encompasses the following procedures | | | |
| wash monkey cell cultures | — | — | 9 |
| add disrupted microcapsules, washes to monkey cells | — | — | 10 |
| wash and incubate cells | — | — | 11 |
| count viral plaques in cell cultures | — | — | 12 |

The results of placebo (spermine alginate microcapsules), virus (WC-3 encapsulated in spermine alginate microcapsules) and control (unencapsulated WC-3) titrations are summarized in the following table:

| Titration Data as pfu/mL | | | | | | |
|---|---|---|---|---|---|---|
| Date and Type | initial | supernatant (washes) | | | microcapsules | |
| Microbead | suspension | 1 | 2 | 3 | intact | disrupted |
| 92 12 03 | | | | | | |
| spermine alginate | | | | | | |
| control | 5,400,000 | | | | | |
| virus | 150,000 | 10,000 | 680 | 650 | 220 | 140,000 |
| placebo | N.A. | 30,000 | 8,700 | 660 | 450 | 180 |

Preliminary tests using control, viral microcapsules and placebo microcapsules showed that infectivity and immunogenicity of the virus was retained after encapsulation and that a substantial fraction of the viral charge was retained in the microcapsules after repeated washings. The efficiency of capture of vaccinia virus exceeded that of rotavirus. Both retained infectivity.

EXAMPLE 8

Mice: 8–12 week-old C57BL/6 (H-$2^b$ haplotype) mice and CD2 (Fl) suckling mice (purchased from Taconic Breeding Laboratories (Germantown, N.Y.) were housed in separate isolation units. Sera from adults and dams were tested for the presence of rotavirus-specific antibodies by ELISA, and only seronegative animals were used in these experiments.

Cells: Fetal green monkey-kidney cells (MA-104) were grown as described in Offit, P. A., et al. 1983 *Infect. Immun.* 42:293–300.

Virus: Bovine rotavirus strain WC3 was isolated in our laboratory as described in Clark, H F., et al. 1986 *Am. J. Dis. Child.* 140:350–356. Simian strain RRV (MMU 18006) was obtained from Nathalie Schmidt (Viral and Rickettsial Disease Laboratory, Berkeley, Calif.). Plaque-purified stocks of rotavirus for use in these studies were prepared in MA-104 cells. Rotaviruses were grown, purified, quantitated by spectrophotometry and titered for infectivity by plaque assay as described in Offit, P. A., et al. 1983 *Infect. Immun.* 42:293–300 and Offit, P. A., et al. 1983 *J. Virol. Methods* 7:29–40.

Selection of anionic polymers and amines to form microcapsules: The anionic polymers tested as their sodium salts were alginic acid (Fisher Scientific Co., Fairlawn, N.J.), polyacrylic acid and cellulose sulfate (Aldrich Chemical Co., St. Louis, Mo.), cellulose acetate phthalate (Eastman Organic Chemicals, Rochester, N.Y.), Carbomer USP (Carbopol 934®, B. F. Goodrich, Cleveland, Ohio), carboxymethylcellulose USP (medium viscosity, Ruger Chemical Co. Inc., Irvington, N.J.)), Heparin USP (The Upjohn Co., Kalamazoo, Mich.), and arabic acid isolated according to the method of U.S. Pat. No. 2,666,759. The anionic polymers which constitute the principal structural component of the microcapsular walls were chosen to provide a range of spacing between nearest neighboring carboxylate groups. Thus, in the extended theta forms of polymers the interanionic distances approximated the equivalent of two methylene groups in polyacrylic acid, six in alginic acid and cellulose sulfate, ten in carboxymethyl cellulose and twenty to thirty in highly branched arabic acid.

With the exception of octadecylamine used as the acetate (Sigma Chemical Co., St. Louis, Mo.), the following amines were tested as their hydrochloride salts: arginine, dodecylamine, and piperazine (Sigma Chemical Co., St. Louis, Mo.), ethylenediamine, triethylamine and triethylenetetraamine (Aldrich Chemical Co., St. Louis, Mo.), and methylene blue (Fisher Scientific Co., Fairlawn, N.J.) The bases were chosen to provide from one to four reactive primary, secondary or tertiary amino groups per molecule and thus, in the instances of polyfunctional amines, to allow formation of multiple salt bridges between and within acidic polymer chains.

Effect of various anionic polymers and amines on rotavirus infectivity: A cell culture stock of bovine rotavirus strain WC3 ($5.0\times10^8$ pfu/ml) was diluted 1:50 in either 0.9% NaCl, the aqueous 0.05N sodium salt of an anionic polymer, or the aqueous 0.05M salt of the amine (adjusted to pH 7.0). Mixtures were titrated for their effect on rotavirus infectivity by plaque assay.

Capacity of water-soluble polymers and amines to form microcapsules and resist breakdown in simulated gastric acid: Polymers and amines which did not inactivate rotavirus were tested in combination to determine their capacity to form microcapsules that resisted breakdown in simulated gastric acid. Six water-soluble anionic polymers were tested in combination with 7 aqueous amines (42 possible combinations). Initially, 1 ml of the aqueous sodium salt of anionic polymer was added dropwise to 1 ml of aqueous amine hydrochloride (or acetate) to determine the capacity to form an interfacial precipitate. Combinations which generated solid material were then used to make microcapsules. Microcapsules were formed by dispersion of the sodium salt of anionic polymer as droplets approximately 5 μm in size into an aqueous solution of the amine salt in a manner analogous to that previously described for preparing calcium alginate microcapsules (U.S. Pat. No. 4,744,933). Short-term stability of microcapsules was tested by observation at room temperature for 5 days in aqueous solution. Microcapsules stable at room temperature were treated with simulated gastric acid (pH 1.2) at 37° C. for 2 hours.

Combinations of acidic polymers and amines which provided stable mono- or oligo-dispersed microcapsules were optimized by varying the ratio of chemical equivalents of amine to equivalents of acidic repeat units of the polymer in the range from 32:1 through 1:32. Reactant ratios which provided maximal settled volumes of microcapsules were selected.

Size of microcapsules was determined by comparison with latex beads of known size (Duke Scientific Corp., Palo Alto, Calif.) by light microscopy.

Capacity of sodium alginate-spermine hydrochloride microcapsules to capture infectious virus: A 5 ml aliquot of a clarified cell culture stock ($6\times10^6$ pfu/ml) of WC3 was added to 5 ml of 0.68 mM sodium alginate and dispersed as droplets nominally 5 μm in size into 20 ml of 0.55 mM spermine hydrochloride. Putative rotavirus-containing microcapsules were centrifuged at 600 xg, washed several times with distilled water and disrupted with 8.0 M sodium phosphate (pH 7.0). Supernatant fluids from washes and fluids obtained after disruption (of putative, rotavirus-containing microcapsules) were tested for the presence of infectious virus by plaque assay. To determine whether virus released in the above experiment was present on the surface or within the matrix of microcapsules, $3\times10^7$ pfu of cell culture-derived WC3 (in a volume of 1 ml) was added to preformed spermine-alginate microcapsules which did not contain virus (placebo beads). Virus was allowed to adsorb for 30 minutes at room temperature. Placebo beads to which virus had been added were washed and disrupted and supernatant fluids were tested for the presence of infectious virus as described above.

Determination of core loading and core loading efficiency of microencapsulation process: The quantity of rotavirus antigen contained within microcapsules was determined by ELISA. Briefly, individual wells of 96-well, flat-bottomed plates (Costar) were coated overnight with 100 µl of a guinea pig anti-WC3 hyperimmune antisera diluted 1:1,000 in 1.5 mM $Na_2CO_3$ and 3.5 mM $NaHCO_3$. Wells were washed five times with buffer containing 1.73 M NaCl, 0.03 M $KH_2PO_4$, 0.13 M $Na_2HPO_4$, and 0.025% Tween 20 in distilled $H_2O$ (washing buffer). 200 µl of buffer containing 0.50 (v/v) gelatin and 0.05% Tween 20 in PBS (blocking buffer) were added to each well. Wells were washed three times with washing buffer and twice with distilled $H_2O$ and 100 µl of fluid from disrupted, rotavirus-containing microcapsule preparations were added to each well and incubated for 1 h at room temperature. Wells were washed five times with washing buffer and 100 µl of rabbit anti-WC3 hyperimmune antisera were added to each well and incubated for 1 h at room temperature. Wells were washed five times with washing buffer and 100 µl of a 1:2,000 dilution (in 1% BSA) of phosphatase-conjugated goat anti-rabbit IgG (Organon Teknika, Durham, N.C.) were added to each well and incubated for 1 h at room temperature. Following five washes with washing buffer, 100 µl of 1 M diethanolamine plus 0.1% (wt/wt) p-nitrophenyl phosphate were added to each well and plates were agitated for 1 h at 37° C. at 140 rpm. 50 µl of disodium ethylenediaminetetraacetic acid were added to each well and calorimetric changes were assayed at 450 nm on a Microplate reader 2000 (BioWhittaker, Walkersville, Md.). Rotavirus antigen concentrations were determined by comparison with a standard curve generated using purified rotavirus of known concentration.

Inoculation of mice with rhodamine-labeled microcapsules and distribution of microcapsules within gut-associated lymphoid tissue (GALT): Rhodamine isothiocyanate (RITC, Sigma Chemical Co., St. Louis, Mo.) at a concentration of 1 mg/ml in 50 mM sodium bicarbonate buffer (pH 9.5) was conjugated to sodium alginate (1% solution in distilled water) after mixture in equal volumes; the reaction was carried out in the dark for 2 h at room temperature. Sodium alginate-RITC was then dialyzed to extinction with distilled water, and used in the formation of spermine-alginate micro-capsules. The RITC-labeled microcapsules were washed 5 times with distilled water prior to use.

Eight-week-old female CS7BL/6 mice were orally inoculated with 20 mg of rhodamine-labeled microcapsules or 20 mg of rhodamine-labeled sodium alginate by proximal esophageal intubation. Two mice were sacrificed from each group 1, 4, 7, 14, 21, and 28 days after inoculation and the Peyer's patches (PP), mesenteric lymph nodes (MLN), and spleens were removed and manually disrupted. (Splenic erythrocytes were lysed in AKC medium (0.16 M $NH_4Cl$, 0.01 M $KHCO_3$, pH 7.2). Cells from all tissues were centrifuged for 5 min at 600 xg, washed three times in RPMI 1640 (GIBCO, Gaithersburg, Md.) and passed through a column of sterile nonabsorbent cotton. $1\times10^4$ cells from each tissue (in a volume of 100 l) was centrifuged onto a microscope slide using the Cytospin 2 (Shandon Inc., Pittsburgh, Pa.) at a speed of 1200 rpm for 5 min. Slides were air-dried for 24 h, and the frequency of rhodamine-labeled cells in each cell population was determined by fluorescence microscopy at a wavelength of 520 nm (Dialux 20, Leitz, Germany).

Uptake of rhodamine-labeled microcapsules by peritoneal exudate cells: Peritoneal exudate cells were obtained from adult C57BL/6 mice after intraperitoneal inoculation with 5 ml of RPMI 1640 medium. Exudate cells were washed twice in RPMI 1640 and resuspended at a concentration of $1\times10^5$ cells per ml in RPMI 1640 containing 10% FBS. $1\times10^4$ cells were incubated with approximately 5 mg of rhodamine-labeled spermine-alginate microcapsules for 10 min at 37° C. in a 5% $CO_2$ incubator. Cells were washed twice with PBS and stained with a 1:100 dilution in PBS of anti-MAC 1 (anti-CD11b) antibody conjugated with fluorescein isothiocyanate (Boehringer Mannheim, Indianapolis, Ind.) for 1 h at room temperature. Cells were washed in PBS, mounted in glycerol-PBS (Citifluor, Citifluor Ltd., London, U.K.), and examined by fluorescence microscopy at wavelengths of 580 nm (for detection of fluorescein label) and 520 nm (for detection of rhodamine label).

Detection of intracellular rotavirus-specific proteins within GALT by indirect immunofluorescence after inoculation of mice with rotavirus-containing microcapsules or free virus: Two groups of four 8-week-old C57BL/6 mice were orally inoculated with approximately $1\times10^7$ pfu per mouse of either free or microencapsulated-WC3 virus. Pairs of mice from each group were sacrificed 1 or 4 days after inoculation and PP, MLN, and spleens were removed. Cells from these tissues were collected and centrifuged onto microscope slides as described above. Slides were fixed in methanol for 10 min, air-dried, and incubated for 1 h with 100 µl of a rabbit polyclonal hyperimmune anti-WC3 serum diluted 1:2,500 in PBS. Slides were washed with PBS and incubated for 1 h with 100 µl of fluorescein-conjugated swine anti-rabbit immunoglobulin (Dako corporation, Carpenteria, Calif.) diluted 1:100 in PBS. Slides were washed with PBS, mounted with glycerol-PBS, and examined by fluorescence microscopy.

Detection of rotavirus-specific antibodies by ELISA after oral or parenteral inoculation of mice with microencapsulated or free virus: Groups of 2–4 mice were 1) intraperitoneally inoculated with $5\times10^4$ or $1\times10^4$ pfu per mouse of microencapsulated WC3 rotavirus or free WC3, 2) orally inoculated with $2.5\times10^6$ or $6.25\times10^5$ pfu per mouse of microencapsulated WC3 or free WC3, 3) orally inoculated with $6.25\times10^4$ or $1.25\times10^4$ pfu per mouse of microencapsulated RRV rotavirus or free RRV, or 4) orally inoculated with an equivalent volume of mock-infected cell culture supernatant fluid. Three weeks after inoculation sera were obtained by retroorbital capillary plexus puncture and tested for the presence of rotavirus-binding IgG by ELISA as follows: Individual wells of 96-well, flat-bottomed plates were coated with either PBS or with 200 ng of purified WC3 or RRV diluted in PBS in a volume of 100 µl. Plates were stored overnight at 4° C. Plates were washed four times with PBS and 200 µl of 1% BSA diluted in PBS were added to each well and incubated for 1 h at room temperature. Duplicate wells were washed four times with PBS and 100 µl of 2-fold dilutions of antisera (beginning at a 1:100 dilution) were added to each well and incubated for 1 h at room temperature. Wells were washed four times with PBS and 100 µl of horse radish peroxidase-conjugated goat anti-mouse IgG (Southern Biotechnology Associates, Birmingham, Ala.) diluted 1:2,000 in 1% BSA were added to each well and incubated for 1 h at room temperature. Wells were washed four times in PBS and 100 µl of a 0.04% tetramethylbenzedine peroxidase solution (Kierkegaard and Perry, Gaithersburg, Md.) were added and incubated for 5 min. 75 µl of an 85% phosphoric acid solution were added to each well and calorimetric changes were determined at a wave length of 450 nm on a microplate ELISA reader. Sera were considered to be positive if the OD value in virus-coated wells was >0.1 units greater than the OD value of wells not coated with viral antigen.

Results—Effect of various water-soluble anionic polymers and amines on rotavirus: Essentially no effect on rotavirus infectivity was found for alginic acid, cellulose sulfate, cellulose acetate phthalate, Carbopol 934®, carboxymethylcellulose, polyacrylic acid, methylene blue and spermine. A 2.5–10-fold reduction in infectivity was noted for heparin, triethylamine, triethylenetetraamine, arginine, ethylenediamine, and octadecylamine. A 30-fold reduction in infectivity was observed for piperazine, a 300-fold reduction for arabic acid, and a complete ablation of infectivity for dodecylamine.

Capacity of water-soluble polymers and amines to form microcapsules which resist breakdown by simulated gastric acid: Six water-soluble anionic polymers and 7 aqueous amines which showed a minimal effect on rotavirus infectivity were tested in combination (42 possible combinations) for their capacity to form stable, oligo-dispersed microcapsules which resisted breakdown by simulated gastric acid; 14 of the 42 possible combinations of polymers and amines formed microcapsules which were stable in simulated gastric acid. These combinations included methylene blue with either cellulose sulfate or cellulose acetate phthalate, spermine with either alginic acid or cellulose sulfate, triethylenetetraamine with either alginic acid or cellulose sulfate, or octadecylamine with either alginic acid, cellulose sulfate, carboxymethylcellulose, cellulose acetate phthalate, polyacrylic acid, or Carbopol 934®.

Capacity of sodium alginate-spermine hydrochloride microcapsules to capture infectious virus: Microcapsules prepared from sodium alginate and spermine hydrochloride were chosen for further study because 1) neither sodium alginate nor spermine hydrochloride reduced rotavirus infectivity, 2) this combination most readily formed monodispersed microcapsules, and 3) this combination provided the largest volume of capsular material. To determine whether infectious rotavirus was contained within microcapsules, WC3 virus was encapsulated in spermine-alginate microcapsules and the microcapsules were tested for the presence of infectious virus by disruption after several washes. Infectious virus was not detected in supernatant fluids after three washes, but was clearly released upon microcapsule disruption. In addition, to determine whether infectious virus was located within or on the surface of microcapsules, virus was added to preformed microcapsules which were washed and disrupted in a similar manner. Infectious virus was not released after disruption of preformed microcapsules to which virus had been added. Therefore, infectious rotavirus was located within the matrix and not only on the surface of spermine-alginate microcapsules.

Efficiency of encapsulation process, core loading capacity, and physical properties of microcapsules: In three separate experiments we found that 1.0%, 2.0% and 6.3% of the initial quantity of infectious virus was encapsulated within the matrix of spermine-alginate microcapsules. Similarly, 2.0–5.0% of the initial quantity of virus antigen was captured in microcapsules. Therefore, the core loading efficiency was similar for both infectious virus and for virus antigen. The core loading capacity (i.e. the quantity of virus antigen divided by the quantity of bead material (wt/wt)) was approximately 2.0–3.0%. When compared to latex beads of known size by light microscopy, the majority of microcapsules were approximately 2 $\mu$m in size with sizes ranging from 1–10 $\mu$m.

Uptake of rhodamine-labeled microcapsules by peritoneal macrophages: Rhodamine-labeled spermine-alginate microcapsules were detected only in peritoneal exudate cells bearing MAC 1 (CD1 lb) on their surface. Approximately 50% to 60% of all MAC 1-bearing cells in the preparation of peritoneal exudate cells engulfed rhodamine-labeled microcapsules.

Distribution of rhodamine-labeled microcapsules within GALT after oral inoculation of mice: Adult C57BL/6 mice were orally inoculated with approximately 20 mg each of rhodamine-labeled spermine-alginate microcapsules. Rhodamine-labeled microcapsules were detected within cells of the PP, MLN, and spleen until at least 28 days after oral inoculation. The greatest quantity of microcapsules in PP and MLN was detected 4 days after inoculation and in spleen 14 days after inoculation. Rhodamine-labeled cells were not detected in PP, MLN, or spleens of animals orally inoculated with 20 mg each of rhodamine-labeled sodium alginate. Therefore, the presence of rhodamine-labeled cells in GAIT after inoculation with rhodamine-labeled microcapsules was not due to breakdown of microcapsules at the intestinal mucosal surface and absorption of rhodamine-labeled sodium alginate, but rather to active phagocytosis of beads.

Detection of rotavirus-specific proteins within GALT by indirect immunofluorescence after inoculation of mice with rotavirus-containing microcapsules or free virus: Adult C57BL/6 mice were orally inoculated with either free or microencapsulated rotavirus strain WC3 at a dose of $1.0 \times 10^7$ pfu per mouse. 1 and 4 days after inoculation animals were sacrificed and cells from PP, MLN, and spleen were examined for the presence of rotavirus-specific proteins by indirect immunofluorescence. 3–5 cells containing rotavirus-specific proteins were detected per $10^4$ cells obtained from PP, MLN, and spleen both 1 and 4 days after inoculation with microencapsulated virus. Cells containing rotavirus antigen were not detected in lymphoid tissues from animals inoculated with free virus.

Effect of microencapsulation on rotavirus immunogenicity: To determine whether encapsulation of infectious rotavirus enhanced rotavirus immunogenicity, adult C57BL/6 mice were inoculated intraperitoneally with microencapsulated or free RRV and 7-day-old CD2 (Fl) suckling mice were orally inoculated with different doses of either free or microencapsulated WC3 or RRV. Three weeks later sera were obtained and tested for the presence of rotavirus-specific IgG by ELISA. Mock-infected animals consistently had rotavirus-specific IgG titers <1:100. Animals were considered to have a rotavirus-specific immune response if titers were greater than or equal to 1:400 (i.e. at least a 4-fold rise in titers above those detected in mock-infected animals). 3 of 4 animals parenterally inoculated with either $5.0 \times 104$ or $1.0 \times 104$ pfu of microencapsulated WC3, but none of 4 animals inoculated with equivalent doses of free WC3 developed detectable rotavirus-binding IgG. Similarly, 3 of 3 mice orally inoculated with RRV at a dose of $1.25 \times 10^4$ pfu per mouse developed rotavirus-specific IgG as compared to 0 of 4 inoculated with the same dose of free virus. 3 of 4 animals orally inoculated with microencapsulated WC3 at a dose of $6.25 \times 10^5$ pfu per mouse developed rotavirus-specific IgG as compared to 0 of 4 animals inoculated with the same dose of free virus.

This example shows that infectious rotavirus can be microencapsulated using an aqueous-based system. The gentle nature of the charged-film microencapsulation process is more likely to allow for retention of viral epitopes necessary for induction of humoral and cellular immune responses than procedures requiring the use of organic solvents. Several additional characteristics of charged-film microcapsules make them attractive for use as antigen delivery systems. First, microcapsules are prepared in aqueous media from materials generally regarded as safe and biodegradable. Sodium alginate, a gelling polysaccharide extracted from kelp, is commonly used in ice creams, soft drinks, and salad dressings as a stabilizer and thickening agent. Spermine, a derivative of spermidine, is a polyamine found in virtually all mammalian cells. Second, microcapsules can be prepared to resist degradation by gastric acid. Third, microcapsules have an internal volume fraction which allows for efficient capture of antigen.

It was found that core loading capacities for rotavirus antigen of 2.0–3.0% as compared to approximately 1% for influenza protein-containing PLCG microcapsules. Fourth, microencapsulation is accomplished at or below room temperature; unencapsulated infectious virus can be readily recovered. Lastly, microcapsules are easily lyophilized, inexpensively made, easily adapted to commercial scale-up and can be prepared sterilely.

When administered to mice, the greatest number of fluorescent spermine-alginate microcapsules were detected in PP and MLN 4 days after oral inoculations and in spleen 14 days after inoculation. These findings are almost identical to those previously described in mice orally inoculated with PLCG microcapsules (Eldridge, J. H., et al. 1989 *Curr. Top. Microbiol. Immunol.* 146:59–66; Eldridge, J. H. et al. 1990 *J. Controlled Release* 11:205–214; Eldridge, J. H., et al. 1991 *Mol. Immunol.* 28:287–294). Uptake of PLCG microcapsules into PP was dependent upon the size and hydrophobicity of microcapsules. PLCG microcapsules larger than 10 μm in diameter were not taken up by M cells and internalized into PP. PLCG microcapsules with diameters ranging from 5 to 10 μm were only detected in PP and those with diameters <5 μm were detected in PP, MLN and spleen. The average size of spermine-alginate microcapsules (i.e. 2 μm) is consistent with uptake of beads into PP, MLN and spleen.

Fluorescent spermine-alginate microcapsules are probably taken up by macrophages within PP. Detection of rhodamine-labeled microcapsules within only those peritoneal exudate cells bearing MAC 1 (CD11b) on their surface supports this. Similarly, macrophages engulf PLCG microcapsules as determined by the presence of MAC 1 on the surface of cells containing fluorescein-labeled PLCG microcapsules. Whether macrophages containing microcapsules within PP migrate to MLN and spleen or free microcapsules travel via lymphatics to MLN and via the bloodstream to the spleen (where they are engulfed by local macrophages) remains to be determined. Macrophages account for approximately 5–9% of all cells within PP. Therefore, our detection of rhodamine-labeled spermine-alginate microcapsules in up to 1.8% of all cells within PP indicates that microcapsules may be taken up by 20–35% of available macrophages.

Rotavirus-specific proteins were detected in GALT of mice orally inoculated with microencapsulated rotavirus but not free virus. Detection of rotavirus-specific proteins after inoculation with microencapsulated virus is consistent with delivery to antigen-presenting cells (which take up beads) of larger quantities of virus than is taken up after inoculation with free virus. However, the quantity of free virus inoculated in these-experiments was adequate to induce a humoral immune response. The inability to detect rotavirus-specific proteins within GALT antigen-presenting cells (in animals inoculated with free virus) probably reflects the fact that antigen is generated in quantities too small or in numbers of cells too few to be detected after heterologous host virus infection. Rotavirus-specific antigens were detected in GALT after oral inoculation of suckling mice with homologous host (i.e. murine) rotaviruses.

Oral or parenteral inoculation of mice with microencapsulated rotaviruses induced a virus-specific antibody response which was of greater magnitude than that induced after inoculation with the same dose of free virus.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departing from the scope of the appended claims.

What is claimed is:

1. A process for preparing a microcapsule comprising an aqueous core surrounded by a capsular wall, said capsular wall comprising a Lewis salt of an amine and an anionic polymer, said process comprising the steps of:

a) selecting a water soluble a anionic polymer, or water soluble salt thereof, and a water soluble amine, or water soluble salt thereof, said anionic polymer and said amine being selected from pairs of anionic polymer and amine having the property that when droplets of an aqueous liquid solution of the anionic polymer are introduced into an aqueous liquid solution of said amine, stable microcapsules of the amine salt of the anionic polymer are formed;

b) dissolving said anionic polymer, or salt thereof, in water to form an anionic polymer liquid solution;

c) dissolving said amine, or salt thereof, in water to form an amine liquid solution;

d) dissolving or suspending an active ingredient in said anionic polymer liquid solution of step b) so that a liquid composition is formed;

e) forming a droplet of said liquid composition resulting from step d);

f) adding said droplet of said liquid composition to said amine liquid solution; and g) allowing said droplet of said liquid composition and said amine liquid solution to react at their mutual interface boundary to form said microcapsule.

2. The process according to claim 1 wherein said anionic polymer is selected from the group consisting of alginic acids, alginic acids linked to a fluorophore, arabic acid, cellulose sulfate, carbokymethylcellulose, carrageenans, chondroitin sulfate, heparin, polyacrylic acid, polyoxyethylene cross-linked polyacrylic acid and polyvinylcarboxylic acid.

3. The process according to claim 1 wherein the amine is selected from the group consisting of arginine, decylamine, dodecylamine, ethylenediamine, piperazine, methylene blue, octadecylamine, triethylamine, triethylenetetramine and spermine.

4. The process according to claim 1 wherein said microcapsule has a particle size between 0.1 and 2,000 microns.

5. The process according to claim 1 wherein, in step d), said active ingredient is suspended in said anionic polymer liquid solution.

6. The process according to claim 5 wherein the active ingredient is a drug.

7. The process according to claim 5 wherein said active ingredient is an immunogenic substance.

8. The process according to claim 7 wherein the immunogenic substance is a viral particle.

9. The process according to claim 7 wherein said immunogenic substance is a rotavirus.

10. The process according to claim 2 wherein said anionic polymer liquid solution has a viscosity of at least 2.5 centipose.

* * * * *